US009062305B2

(12) United States Patent
Tsui et al.

(10) Patent No.: US 9,062,305 B2
(45) Date of Patent: Jun. 23, 2015

(54) **GENERATION OF HUMAN *DE NOVO* PIX PHAGE DISPLAY LIBRARIES**

(75) Inventors: Ping Tsui, Berwyn, PA (US); Lei Shi, Radnor, PA (US); Jin Lu, Radnor, PA (US); John Wheeler, Radnor, PA (US); Brian Whitaker, Radnor, PA (US); Lionella Borozdina-Birch, San Diego, CA (US); Juan C. Almagro, Radnor, PA (US); Bernard Amegadzie, Radnor, PA (US); Mark Tornetta, Radnor, PA (US); Ramachandra Reddy, Radnor, PA (US); David M. Knight, Radnor, PA (US); Jinquan Luo, Radnor, PA (US); Raymond W. Sweet, Radnor, PA (US); Qiang Chen, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 1091 days.

(21) Appl. No.: 12/546,850

(22) Filed: Aug. 25, 2009

(65) Prior Publication Data
US 2010/0021477 A1 Jan. 28, 2010

Related U.S. Application Data

(63) Continuation-in-part of application No. PCT/US2008/084255, filed on Nov. 21, 2008.

(60) Provisional application No. 61/014,786, filed on Dec. 19, 2007.

(51) Int. Cl.
*C40B 30/04* (2006.01)
*C12N 15/10* (2006.01)
*C40B 40/02* (2006.01)

(52) U.S. Cl.
CPC ............. *C12N 15/1037* (2013.01); *C40B 30/04* (2013.01); *C40B 40/02* (2013.01)

(58) Field of Classification Search
None
See application file for complete search history.

(56) References Cited

U.S. PATENT DOCUMENTS

| 5,658,727 A | 8/1997 | Barbas et al. |
| 6,670,127 B2 | 12/2003 | Evans |
| 2003/0186322 A1 | 10/2003 | Janda et al. |

FOREIGN PATENT DOCUMENTS

WO WO 2006/050280 A2 5/2006

OTHER PUBLICATIONS van den Beucken et al. (Jun. 2, 2003) FEBS Letters vol. 546 pp. 288 and 294.*
Barbas et al. (Oct. 1995) Methods vol. 8 pp. 94 to 103.*
(Continued)

*Primary Examiner* — Christian Boesen
(74) *Attorney, Agent, or Firm* — Brian C. Carey

(57) ABSTRACT

Described and claimed herein are combinatorial synthetic Fab libraries displayed on a phage pIX protein. The libraries were built on scaffolds representing the most frequently used genes in human antibodies, which were diversified to mirror the variability of natural antibodies. After selection using a diverse panel of proteins, numerous specific and high-affinity Fabs were isolated. By a process called in-line maturation the affinity of some antibodies was improved up to one hundred-fold yielding low pM binders suitable for in vivo use. This work thus demonstrates the feasibility of displaying complex Fab libraries as pIX-fusion proteins for antibody discovery and lays the foundations for studies on the structure-function relationship of antibodies.

1 Claim, 30 Drawing Sheets

(56) References Cited

OTHER PUBLICATIONS

Kunkel et al., "Efficient Site-Directed Mutagenesis Using Uracil-Containing DNA", Methods in Enzymology, Academic Press Inc. San Diego, CA US, vol. 204, pp. 125-139 XP009073170 (1991).
Gao et al., "A cell-penetrating peptide from a novel pVII-pIX phage-displayed random peptide library", Bioorganic & Medicinal Chemistry, Pergamon, GB, vol. 10, No. 12, pp. 4057-4065 (2002).
Kawsnikowski et al., "Mutlivalent display system on filamentous bacteriophage pVII minor coat protein", Journal of Immunilogical Methods, Elseiver Science Publishers, B.V. Amsterdam NL, vol. 307, No. 1-2, pp. 135-143 XP005221142 (2005).
Endemann and Model, J. Mol. Biol., 250: pp. 496-506, 1995.
Gao et al., Proc. Natl Acad. Sci USA, 96: pp. 6025-6030, 1999.
Gao et al., Proc Natl. Acad. Sci USA, 99: pp. 12612-12616, 2002.
Chothia et al., J. Mol. Biol., 227: pp. 799-817, 1992.
Tomlinson et al., EMBRO J.,14: pp. 4628-4638, 1995.
Williams et al., J. Mol. Biol, 264: pp. 220-232, 1996.
Rothe et al., J. Mol. Biol. 376: pp. 1182-1200, 2008.
de Wildt et al., Nat. Biotechnol 18: pp. 989-994, 2000.
Lee et al., J. Mol. Biol. 340: pp. 1073-1093, 2004.
Söderlind et al., Nat. Biotechnol 18: pp. 852-856, 2000.
Hoet et al., Nat. Biotechnol 23: pp. 344-348, 2005.
Marks et al., J. Mol. Biol, 222: pp. 581-597, 1991.
Griffiths et al., EMBO J. 13: pp. 3245-3260, 1994.
Tsui et al., J. Immunolo Meth. 263: pp. 123-132, 2002.
Kunkel, Proc. Nat. Acad. Sci, 82: pp. 448, 1985.
Stemmer et al., Gene, 164: pp. 49-53, 1995.
Crooks et al., Genome Research, 14: pp. 1188-1190, 2004.
Wang & Saven Nucleic Acids Res 30: e120, 2002.
Almagro, J. Mol Recognit, 17: pp. 132-143, 2004.
Hoogenboom, Nat. Biotechnol 23: pp. 1105-1116, 2005.
de Wildt et al., J. Mol. Biol. 285: pp. 895-901, 1999.
Persson et al., J. Mol. Biol. 357: pp. 607-620, 2006.
Cobaugh et al., J. Mol. Biol. 378: pp. 622-633, 2008.
Xiabing MA, "Construction of human natural Fab fragment phage antibody library and preliminary screening of anti-gp96 antibody", Medical Pharmaceutical and Hygienic Collections, vol. 9, p. 32-45 (2006) (Abstract Only).
Dehaard H J et al., "A large non-immunized human Fab fragment phage library that permits rapid isolation and kinetic analysis of high affinity antibodies", Journal of Biological Chemistry, American Society for Biochemistry and Molecular Biology, US, vol. 274, No. 26, pp. 18218-18230, Jun. 25, 1999 XP002128301.
Oh et al., Enhancing phage display of antibody fragments using gIII-amber suppression:, Gene, Elsevier, Amsterdam, NL, vol. 386, No. 1-2, pp. 81-89 Dec. 19, 2006 XP005808302.

* cited by examiner

FIGURE 2

APTEC*STSGGGGS*MSVLVYSFASFVLGWCLRSGITYFTRLME (SEQ ID NO: 79)

FIGURE 6

H-CDR3

95- (D) (N)n(N+Y)m(F)DY -101

The H-CDR3 pattern is highlighted in bold underlining. The variable amino acids are shown in parentheses.

Where:

(D)   = The Asp (D) and Gly (G) rich position.

(N)n  = Ala (A) and Gly (G) rich position. n = 3-7.

(Y)m  = Same as (N) except also rich in Y (Tyr). m= 1-4.

(F)   = The Phe (F) dominant position.

FIGURE 7

| H-CDR3 length | 95 95a 95b 95c 95d 95e 95f 95g 96 97 98 |
|---|---|
| 7 | nns - - - - - - - nns nns nns |
| 8 | nns nns - - - - - - nns nns nns |
| 9 | D N N - - - - - N N N |
| 10 | D N N N - - - - N N N |
| 11 | D N N N N - - - N N N+Y |
| 12 | D N N N N N+Y - - N+Y N+Y N+Y |
| 13 | D N N N N N N - N+Y N+Y N+Y |
| 14 | D N N N N N N N N+Y N+Y |

Oligo compositions at D position:

1: [ACGT]= [15-15-68-2]

2: [ACGT]= [43-11-33-13]

3: [ACGT]= [2-29-24-45]

Oligo compositions at N position:

1: [ACGT]= [19-14-41-26]

2: [ACGT]= [28-25-33-14]

3: [ACGT]= [0-34-36-30]

nns are IUB codons.

FIGURE 8
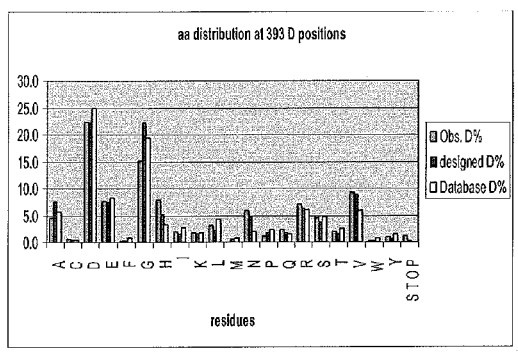
FIG. 8A
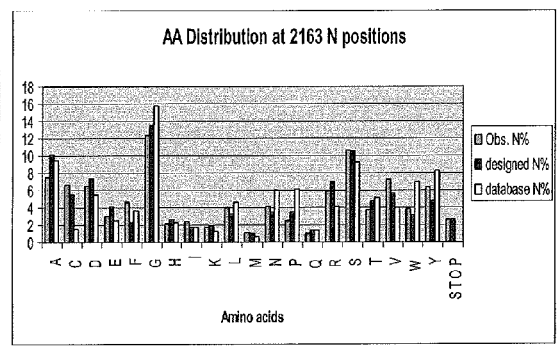
FIG. 8B
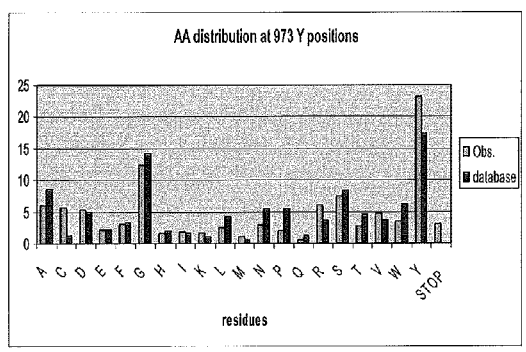
FIG. 8C
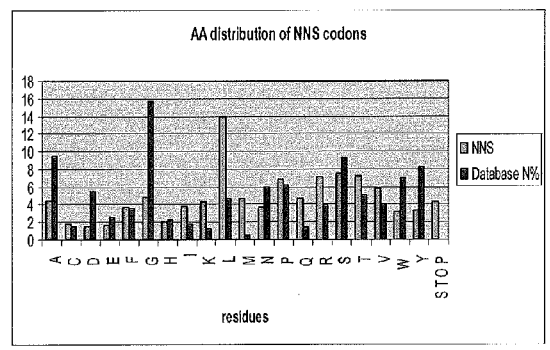
FIG. 8D

**V2 library Organization
(One of the 16 sets of the Fabs)**

FIGURE 15

| Fab ID: | Sequence: |
|---|---|
| Hc/Lc | Heavy Chain/Light Chain |
| 169/A27 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:18)<br><br>EIVLTQSPGTLSLSPGERATLSCRASQSVSSSYLAWYQQKPGQAPRLLIYGASSRATGIPDRFSGSGSGTDF TLTISRLEPEDFAVYYCQQYGSSPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLSPVTKSFNR GEC (SEQ ID NO:19) |
| 169/012 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:20)<br><br>DIQMTQSPSSLSASVGDRVTITCRASQSISSYLNWYQQKPGKAPKLLIYAASSLQSGVPSRFSGSGSGTDF TLTISSLQPEDFATYYCQQSYSTPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLPVTKSFNR GEC (SEQ ID NO:21) |

FIGURE 15 CONT'D.

| Fab ID: Hc/Lc | Sequence: Heavy Chain/Light Chain |
|---|---|
| 169/L6 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:22)<br><br>EIVLTQSPATLSLSPGERATLSCRASQSVSSYLAWYQQKPGQAPRLLIYDASNRATGIPARFSGSGSGTDF TLTISSLEPEDFAVYYCQQRSNWPLTFGQGTKVEIKRTVAAPSVFIFPPSDEQLKSGTASVVCLLNNFYPR EAKVQWKVDNALQSGNSQESVTEQDSKDSTYSLSSTLTLSKADYEKHKVYACEVTHQGLSLPVTKSFN RGEC (SEQ ID NO:23) |
| 169/B3 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:24)<br><br>DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSLP VTKSFNRGEC (SEQ ID NO:25) |
| 323/A27 | EVQLLESGGGLVQPGGSLRLSCAASGFTFSSYAMSWVRQAPGKGLEWVSAISGSGGSTYYADSVKGRFT |

FIGURE 15 CONT'D.

| Fab ID: | Sequence: |
|---|---|
| Hc/Lc | Heavy Chain/Light Chain |
|  | ISRDNSKNTLYLQMNSLRAEDTAVYYCAKQLWGYYALEIWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNHKP SNTKVDKKVEPKSCDKTHT (SEQ ID NO:26) |
|  | EIVLTQSPGTLSLSPGERATLSCRASQSVSSSYLAWYQQKPGQAPRLLIYGASSRATGIPDRFSGSGSGTDF TLTISRLEPEDFAVYYCQQYGSSPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLPVTKSFNR GEC (SEQ ID NO:27) |
| 323/012 | EVQLLESGGGLVQPGGSLRLSCAASGFTFSSYAMSWVRQAPGKGLEWVSAISGSGGSTYYADSVKGRFT ISRDNSKNTLYLQMNSLRAEDTAVYYCAKQLWGYYALEIWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNHKP SNTKVDKKVEPKSCDKTHT (SEQ ID NO:28) |
|  | DIQMTQSPSSLSASVGDRVTITCRASQSISSYLNWYQQKPGKAPKLLIYAASSLQSGVPSRFSGSGSGTDF TLTISSLQPEDFATYYCQQSYSTPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLPVTKSFNR GEC (SEQ ID NO:29) |
| 323/L6 | EVQLLESGGGLVQPGGSLRLSCAASGFTFSSYAMSWVRQAPGKGLEWVSAISGSGGSTYYADSVKGRFT ISRDNSKNTLYLQMNSLRAEDTAVYYCAKQLWGYYALEIWGQGTLVTVSSASTKGPSVFPLAPSSKSTS |

FIGURE 15 CONT'D.

| Fab ID: Hc/Lc | Sequence: Heavy Chain/Light Chain |
|---|---|
| | GGTAALGCLVKDYFPEPVTVSWNSGALTSGVHTFPAVLQSSGLYSLSSVVTVPSSSLGTQTYICNVNHKP SNTKVDKKVEPKSCDKTHT (SEQ ID NO:30) |
| | EIVLTQSPATLSLSPGERATLSCRASQSVSSYLAWYQQKPGQAPRLLIYDASNRATGIPARFSGSGSGTDF TLTISSLEPEDFAVYYCQQRSNWPLTFGQGTKVEIKRTVAAPSVFIFPPSDEQLKSGTASVVCLLNNFYPR EAKVQWKVDNALQSGNSQESVTEQDSKDSTYSLSSTLTLSKADYEKHKVYACEVTHQGLSLPVTKSFN RGEC (SEQ ID NO:31) |
| 323/B3 | EVQLLESGGGLVQPGGSLRLSCAASGFTFSSYAMSWVRQAPGKGLEWVSAISGSGGSTYYADSVKGRFT ISRDNSKNTLYLQMNSLRAEDTAVYYCAKQLWGYYALEIWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNHKP SNTKVDKKVEPKSCDKTHT (SEQ ID NO:32) |
| | DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSLP VTKSFNRGEC (SEQ ID NO:33) |
| 353/A27 | VQLVETGGGLIQPGGSLRLSCAASGFTVSSNYMSWVRQAPGKGLEWVSVIYSGGSTYYADSVKGRFTIS RDNSKNTLYLQMNSLRAEDTAVYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS |

FIGURE 15 CONT'D.

| Fab ID: | Sequence: |
|---|---|
| Hc/Lc | Heavy Chain/Light Chain |
| | NTKVDKKVEPKSCDKTHT (SEQ ID NO:34) |
| | EIVLTQSPGTLSLSPGERATLSCRASQSVSSSYLAWYQQKPGQAPRLLIYGASSRATGIPDRFSGSGSGTDF TLTISRLEPEDFAVYYCQQYGSSPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLPVTKSFNR GEC (SEQ ID NO:35) |
| 353/012 | VQLVETGGGLIQPGGSLRLSCAASGFTVSSNYMSWVRQAPGKGLEWVSVIYSGGSTYYADSVKGRFTIS RDNSKNTLYLQMNSLRAEDTAVYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:36) |
| | DIQMTQSPSSLSASVGDRVTITCRASQSISSYLNWYQQKPGKAPKLLIYAASSLQSGVPSRFSGSGSGTDF TLTISSLQPEDFATYYCQQSYSTPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLPVTKSFNR GEC (SEQ ID NO:37) |
| 353/L6 | VQLVETGGGLIQPGGSLRLSCAASGFTVSSNYMSWVRQAPGKGLEWVSVIYSGGSTYYADSVKGRFTIS RDNSKNTLYLQMNSLRAEDTAVYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:38) |

FIGURE 15 CONT'D.

| Fab ID: | Sequence: |
|---|---|
| Hc/Lc | Heavy Chain/Light Chain |
| | EIVLTQSPATLSLSPGERATLSCRASQSVSSYLAWYQQKPGQAPRLLIYDASNRATGIPARFSGSGSGTDF TLTISSLEPEDFAVYYCQQRSNWPLTFGQGTKVEIKRTVAAPSVFIFPPSDEQLKSGTASVVCLLNNFYPR EAKVQWKVDNALQSGNSQESVTEQDSKDSTYSLSSTLTLSKADYEKHKVYACEVTHQGLSLPVTKSFN RGEC (SEQ ID NO:39) |
| 353/B3 | VQLVETGGGLIQPGGSLRLSCAASGFTVSSNYMSWVRQAPGKGLEWVSVIYSGGSTYYADSVKGRFTIS RDNSKNTLYLQMNSLRAEDTAVYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:40) |
| | DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSLP VTKSFNRGEC (SEQ ID NO:41) |
| 551/A27 | EVQLVQSGAEVKKPGESLKISCKGSGYSFTSYWIGWVRQMPGKGLEWMGIIYPGDSDTRYSPSFQGQVT ISADKSISTAYLQWSSLKASDTAMYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:42) |

FIGURE 15 CONT'D.

| Fab ID: Hc/Lc | Sequence: Heavy Chain/Light Chain |
|---|---|
| | EIVLTQSPGTLSLSPGERATLSCRASQSVSSSYLAWYQQKPGQAPRLLIYGASSRATGIPDRFSGSGSGTDF TLTISRLEPEDFAVYYCQQYGSSPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLPVTKSFNR GEC (SEQ ID NO:43) |
| 551/012 | EVQLVQSGAEVKKPGESLKISCKGSGYSFTSYWIGWVRQMPGKGLEWMGIIYPGDSDTRYSPSFQGQVT ISADKSISTAYLQWSSLKASDTAMYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:44) |
| | DIQMTQSPSSLSASVGDRVTITCRASQSISSYLNWYQQKPGKAPKLLIYAASSLQSGVPSRFSGSGSGTDF TLTISSLQPEDFATYYCQQSYSTPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLPVTKSFNR GEC(SEQ ID NO:45) |
| 551/L6 | EVQLVQSGAEVKKPGESLKISCKGSGYSFTSYWIGWVRQMPGKGLEWMGIIYPGDSDTRYSPSFQGQVT ISADKSISTAYLQWSSLKASDTAMYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT(SEQ ID NO:46) |
| | EIVLTQSPATLSLSPGERATLSCRASQSVSSYLAWYQQKPGQAPRLLIYDASNRATGIPARFSGSGSGTDF |

FIGURE 15 CONT'D.

| Fab ID: Hc/Lc | Sequence: Heavy Chain/Light Chain |
|---|---|
| | TLTISSLEPEDFAVYYCQQRSNWPLTFGQGTKVEIKRTVAAPSVFIFPPSDEQLKSGTASVVCLLNNFYPR EAKVQWKVDNALQSGNSQESVTEQDSKDSTYSLSSTLTLSKADYEKHKVYACEVTHQGLSLPVTKSFN RGEC (SEQ ID NO:47) |
| 551/B3 | EVQLVQSGAEVKKPGESLKISCKGSGYSFTSYWIGWVRQMPGKGLEWMGIIYPGDSDTRYSPSFQGQVT ISADKSISTAYLQWSSLKASDTAMYYCARQLWGYYALEIWGQGTLVTVSSASTKGPSVFPLAPSSKSTSG GTAALGCLVKDYFPEPVTVSWNSGALTSGVHTFPAVLQSSGLYSLSSVVTVPSSSLGTQTYICNVNHKPS NTKVDKKVEPKSCDKTHT (SEQ ID NO:48)<br><br>DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSLP VTKSFNRGEC (SEQ ID NO:49) |

FIGURE 16

| Antigen | Clone | Scaffold | LCDR1 | LCDR2 | LCDR3 | ka (1/Ms)10⁴ | kd (1/s)10⁻⁰⁴ | Kd (pM) |
|---|---|---|---|---|---|---|---|---|
| IgG | F17(Hc/Lc) (SEQ ID NO: 75/76) | 169/L6 | RASQSVADDLA | YASNRAT | QQRIGAPYT | 6.8 | 2.81 | 4000 |
| IgG | F17-21 | 169/L6 | ------KF-- | G------ | --------- | 8.5 | .037 | 43 |
| IgG | F17-22 | 169/L6 | ------ND-- | N------ | --------- | 7.6 | .34 | 453 |
| IgG | F19 (Hc/Lc) (SEQ ID NO: 77/78) | 169/L6 | RASQSVRSYLA | AASNRAT | QQRSGWPIT | 158 | 6.64 | 400 |
| IgG | F19-23 | 169/L6 | ------KF-- | T------ | ---T----- | 325 | 0.79 | 24 |
| IgG | F19-24 | 169/L6 | ------ND-- | D------ | ---T----- | 292 | 1.28 | 44 |
| IgG | F19-25 | 169/L6 | ------DW-- | D------ | ---D----- | 289 | 4.84 | 167 |
| mTF | F10 (Hc/Lc) SEQ ID NO: 73/74) | 169/L6 | RASQSVASWLA | GASNRAT | QQSDGWPYT | | | |
| mTF | F10-33 | 169/L6 | ------D--- | N------ | --------- | 33.6 | 68.9 | 20 |
| mTF | F10-35 | 169/L6 | ------K--- | Y------ | --------- | 5.8 | 3.9 | 6 |
| mTF |  |  |  |  |  | 27.6 | 9.9 | 3 |

FIGURE 17

| Heavy Chain | SEQ ID NO: | Amino Acid Sequence |
|---|---|---|
| 169 | 5 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARQLWGYYALEIWGQGTLVTVSSAS |
| 323 | 6 | EVQLLESGGGLVQPGGSLRLSCAASGFTFSSYAMSWVRQAPGKGLEWVSAISGSGGSTYYADSVKGRFT ISRDNSKNTLYLQMNSLRAEDTAVYYCAKQLWGYYALEIWGQGTLVTVSSAS |
| 353 | 7 | VQLVETGGGLIQPGGSLRLSCAASGFTVSSNYMSWVRQAPGKGLEWVSVIYSGGSTYYADSVKGRFTIS RDNSKNTLYLQMNSLRAEDTAVYYCARQLWGYYALEIWGQGTLVTVSSAS |
| 551 | 8 | EVQLVQSGAEVKKPGESLKISCKGSGYSFTSYWIGWVRQMPGKGLEWMGIIYPGDSDTRYSPSFQGQVT ISADKSISTAYLQWSSLKASDTAMYYCARQLWGYYALEIWGQGTLVTVSSAS |
| Kappa | | |
| A27 | 9 | EIVLTQSPGTLSLSPGERATLSCRASQSVSSSYLAWYQQKPGQAPRLLIYGASSRATGIPDRFSGSGSGTDF TLTISRLEPEDFAVYYCQQYGSSPLTFGQGTKVEIK |
| O12 | 10 | DIQMTQSPSSLSASVGDRVTITCRASQSISSYLNWYQQKPGKAPKLLIYAASSLQSGVPSRFSGSGSGTDF TLTISSLQPEDFATYYCQQSYSTPLTFGQGTKVEIK |
| L6 | 11 | EIVLTQSPATLSLSPGERATLSCRASQSVSSYLAWYQQKPGQAPRLLIYDASNRATGIPARFSGSGSGTDF TLTISSLEPEDFAVYYCQQRSNWPLTFGQGTKVEIK |
| B3 | 12 | DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIK |
| Lambda | | |
| 1b | 13 | VLTQPPSVSAAPGQKVTISCSGSSSNIGNNYVSWYQQLPGTAPKLLIYDNNKRPSGIPDRFSGSKSGTSAT |

FIGURE 17 CONT'D.

| Heavy Chain | SEQ ID NO: | Amino Acid Sequence |
|---|---|---|
| | | LGITGLQTGDEADYYCGTWDSSLSAVVFGGGTKLTVL |
| 1e | 14 | VLTQPPSVSGAPGQRVTISCTGSSNIGAGYDVHWYQQLPGTAPKLLIYGNSNRPSGVPDRFSGS KSGTSASLAITGLQAEDEADYYCQSYDSSLSGVVFGGGTKLTVL |
| 2a2 | 15 | ALTQPASVSGSPGQSITISCTGTSSDVGGYNYVSWYQQHPGKAPKLMIYEVSNRPSGVSNRFSGSKSGN TASLTISGLQAEDEADYYCSSYTSSSTLVVFGGGTKLTVL |
| 3L | 16 | ELTQDPAVSVALGQTVRITCQGDSLRSYYASWYQQKPGQAPVLVIYGKNNRPSGIPDRFSGSSSGNTAS LTITGAQAEDEADYYCNSRDSSGNHFGGGTKLTVL |
| C-lambda | 17 | GQPKAAPSVTLFPPSSEELQANKATLVCLISDFYPGAVTVAWKADSSPVKAGVETTTPSKQSNNKYAAS SYLSLTPEQWKSHRSYSCQVTHEGSTVEKTVAPTECS |

FIGURE 18

| Fab ID HC/Lc | Sequence Heavy Chain/Light Chain |
|---|---|
| BSA-C2 | QVQLVQSGAEVKKPGSSVKVSCKASGGTFSSYAISWVRQAPGQGLEWMGGIIPINGNANYAQKFQGRVTITADESTSTAYMELSSLRSEDTAVYYCARRAGMRVQTYFFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO:55)<br><br>DIVMTQSPDSLAVSLGERATINCKSSQSVLYSSNNKNYLAWYQQKPGQPPLLIYWASTRESGVPDRFSGSGSGTDFTLTISSLQAEDVAVYYCQQYYSTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSLPVTKSFNRGEC (SEQ ID NO:56) |
| BSA-C6 | QVQLVQSGAEVKKPGSSVKVSCKASGGTFSSYGISWVRQAPGQGLEWMGGIIPIFGTANYAQKFQGRVTITADESTSTAYMELSSLRSEDTAVYYCARLCVSPAWDQCFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO:57)<br><br>DIVMTQSPDSLAVSLGERATINCKSSQSVLYSSNNKNYLAWYQQKPGQPPLLIYWASTRESGVPDRFSGSGSGTDFTLTISSLQAEDVAVYYCQQYYSTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSLPVTKSFNRGEC (SEQ ID NO:58) |

FIGURE 18 CONT'D.

| Fab ID HC/Lc | Sequence Heavy Chain/Light Chain |
|---|---|
| BSA-D6 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARGIIGNLVVLDYWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNHKP SNTKVDKKVEPKSCDKTHT (SEQ ID NO:59)<br><br>DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSLP VTKSFNRGEC (SEQ ID NO:60) |
| BSA-D11 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARIRWGGWFRGYLDYWGQGTLVTVSSASTKGPSVFPLAPSSK STSGGTAALGCLVKDYFPEPVTVSWNSGALTSGVHTFPAVLQSSGLYSLSSVVTVPSSSLGTQTYICNVN HKPSNTKVDKKVEPKSCDKTHT (SEQ ID NO:61)<br><br>EIVLTQSPGTLSLSPGERATLSCRASQSVSSSYLAWYQQKPGQAPRLLIYGASSRATGIPDRFSGSGSGTDF TLTISRLEPEDFAVYYCQQYGSSPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLPVTKSFNR GEC (SEQ ID NO:62) |

FIGURE 18 CONT'D.

| Fab ID HC/Lc | Sequence Heavy Chain/Light Chain |
|---|---|
| BSA-F4 | QVQLVQSGAEVKKPGSSVKVSCKASGGTFSSYGISWVRQAPGQGLEWMGGIIPIFGTANYAQKFQGRVT ITADESTSTAYMELSSLRSEDTAVYYCARDFGVYTWLGQTFDYWGQGTLVTVSSASTKGPSVFPLAPSS KSTSGGTAALGCLVKDYFPEPVTVSWNSGALTSGVHTFPAVLQSSGLYSLSSVVTVPSSSLGTQTYICNV NHKPSNTKVDKKVEPKSCDKTHT (SEQ ID NO:63) |
| | EIVLTQSPGTLSLSPGERATLSCRASQSVSSSYLAWYQQKPGQAPRLLIYGASSRATGIPDRFSGSGSGTDF TLTISRLEPEDFAVYYCQQYGSSPLTFGQGTKVEIKRTVAAPSVFIFPPSDEQLKSGTASVVCLLNNFYPRE AKVQWKVDNALQSGNSQESVTEQDSKDSTYSLSSTLTLSKADYEKHKVYACEVTHQGLSLSPVTKSFNR GEC (SEQ ID NO:64) |
| BSA-F6 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCARGIIGTITYVFDYWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNHKP SNTKVDKKVEPKSCDKTHT (SEQ ID NO:65) |
| | DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSLP VTKSFNRGEC (SEQ ID NO:66) |

FIGURE 18 CONT'D.

| Fab ID HC/Lc | Sequence Heavy Chain/Light Chain |
|---|---|
| HEL-E5 | QVQLVQSGAEVKKPGSSVKVSCKASGGTFSSYAISWVRQAPGQGLEWMGWIIPYNGNANYAQKFQGR VTITADESTSTAYMELSSLRSEDTAVYYCARHTPVRDLDYWGQGTLVTVSSASTKGPSVFPLAPSSKSTS GGTAALGCLVKDYFPEPVTVSWNSGALTSGVHTFPAVLQSSGLYSLSSVVTVPSSSLGTQTYICNVNHKP SNTKVDKKVEPKSCDKTHT (SEQ ID NO:67)<br><br>DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSLP VTKSFNRGEC (SEQ ID NO:68) |
| HEL-E7 | QVQLVQSGAEVKKPGSSVKVSCKASGGTFSSYAISWVRQAPGQGLEWMGGIIPIFGTANYAQKFQGRVT ITADESTSTAYMELSSLRSEDTAVYYCAREGGEVYDWEYYLDYWGQGTLVTVSSASTKGPSVFPLAPSS KSTSGGTAALGCLVKDYFPEPVTVSWNSGALTSGVHTFPAVLQSSGLYSLSSVVTVPSSSLGTQTYICNV NHKPSNTKVDKKVEPKSCDKTHT (SEQ ID NO:69)<br><br>DIVMTQSPDSLAVSLGERATINCKSSQSVLYSSNNKNYLAWYQQKPGQPPLLIYWASTRESGVPDRFSGS GSGTDFTLTISSLQAEDVAVYYCQQYYSTPLTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSLP VTKSFNRGEC (SEQ ID NO:70) |

FIGURE 18 CONT'D.

| Fab ID HC/Lc | Sequence Heavy Chain/Light Chain |
|---|---|
| HEL-E8 | QVQLVQSGAEVKKPGSSVKVSCKASGGTFSSYGISWVRQAPGQGLEWMGWIIPIFGTANYAQKFQGRVTITADESTSTAYMELSSLRSEDTAVYYCARDGNPFRYWPFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHT (SEQ ID NO:71)<br><br>DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSLPVTKSFNRGEC (SEQ ID NO:72) |

SEQUENCE LISTING

```
<160> NUMBER OF SEQ ID NOS: 79

<210> SEQ ID NO 1
<211> LENGTH: 54
<212> TYPE: DNA
<213> ORGANISM: Homo sapiens

<400> SEQUENCE: 1
gcgtctcagt ctgttgacta ataaggttaa tcttaaatgc actggtacca gcag         54

<210> SEQ ID NO 2
<211> LENGTH: 54
<212> TYPE: DNA
<213> ORGANISM: Homo sapiens

<400> SEQUENCE: 2
ctgctggtac cagtgcattt aagattaacc ttattagtca acagactgag acgc         54

<210> SEQ ID NO 3
<211> LENGTH: 54
<212> TYPE: DNA
<213> ORGANISM: Homo sapiens
<220> FEATURE:
<221> NAME/KEY: misc_feature
<222> LOCATION: 19, 20, 22, 23, 28, 29, 34, 35
<223> OTHER INFORMATION: n = A,T,C or G

<400> SEQUENCE: 3
gcgtctcagt ctgttgacnn knnkggtnnk tctnnkatgc actggtacca gcag         54

<210> SEQ ID NO 4
<211> LENGTH: 54
<212> TYPE: DNA
<213> ORGANISM: Homo sapiens
<220> FEATURE:
<221> NAME/KEY: misc_feature
```

```
<222> LOCATION: 19, 20, 23, 24, 29, 30, 34, 35
<223> OTHER INFORMATION: n = A,T,C or G

<400> SEQUENCE: 4
gcgtctcagt ctgttgacnn kvnnggtvnn tctnnkatgc actggtacca gcag          54

<210> SEQ ID NO 5
<211> LENGTH: 121
<212> TYPE: PRT
<213> ORGANISM: Homo sapines

<400> SEQUENCE: 5
```

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Leu Trp Gly Tyr Tyr Ala Leu Glu Ile Trp Gly Gln Gly
            100                 105                 110

Thr Leu Val Thr Val Ser Ser Ala Ser
        115                 120

```
<210> SEQ ID NO 6
<211> LENGTH: 121
<212> TYPE: PRT
<213> ORGANISM: Homo sapiens

<400> SEQUENCE: 6
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Leu Trp Gly Tyr Tyr Ala Leu Glu Ile Trp Gly Gln Gly
            100                 105                 110

Thr Leu Val Thr Val Ser Ser Ala Ser
        115                 120

```
<210> SEQ ID NO 7
<211> LENGTH: 119
<212> TYPE: PRT
<213> ORGANISM: Homo sapiens

<400> SEQUENCE: 7
```

```
Val Gln Leu Val Glu Thr Gly Gly Gly Leu Ile Gln Pro Gly Gly Ser
 1               5                  10                  15

Leu Arg Leu Ser Cys Ala Ala Ser Gly Phe Thr Val Ser Asn Tyr
             20                  25                  30

Met Ser Trp Val Arg Gln Ala Pro Gly Lys Gly Leu Glu Trp Val Ser
         35                  40                  45

Val Ile Tyr Ser Gly Gly Ser Thr Tyr Tyr Ala Asp Ser Val Lys Gly
         50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
             85                  90                  95

Gln Leu Trp Gly Tyr Tyr Ala Leu Glu Ile Trp Gly Gln Gly Thr Leu
         100                 105                 110

Val Thr Val Ser Ser Ala Ser
         115
```

```
<210> SEQ ID NO 8
<211> LENGTH: 121
<212> TYPE: PRT
<213> ORGANISM: Homo sapiens

<400> SEQUENCE: 8

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Gln Leu Trp Gly Tyr Tyr Ala Leu Glu Ile Trp Gly Gln Gly
         100                 105                 110

Thr Leu Val Thr Val Ser Ser Ala Ser
         115                 120
```

```
<210> SEQ ID NO 9
<211> LENGTH: 108
<212> TYPE: PRT
<213> ORGANISM: Homo sapiens

<400> SEQUENCE: 9

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80
```

```
Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 11
<211> LENGTH: 107
<212> TYPE: PRT
<213> ORGANISM: Homo sapiens

<400> SEQUENCE: 11

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 12
<211> LENGTH: 112
<212> TYPE: PRT
<213> ORGANISM: Homo sapiens

<400> SEQUENCE: 12

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
```

```
                35                  40                  45
Pro Pro Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Thr Pro Leu Thr Phe Gly Gln Gly Thr Lys Val Glu Ile Lys
            100                 105                 110

<210> SEQ ID NO 13
<211> LENGTH: 108
<212> TYPE: PRT
<213> ORGANISM: Homo sapiens

<400> SEQUENCE: 13

Val Leu Thr Gln Pro Pro Ser Val Ser Ala Ala Pro Gly Gln Lys Val
1               5                   10                  15

Thr Ile Ser Cys Ser Gly Ser Ser Asn Ile Gly Asn Asn Tyr Val
                20                  25                  30

Ser Trp Tyr Gln Gln Leu Pro Gly Thr Ala Pro Lys Leu Leu Ile Tyr
            35                  40                  45

Asp Asn Asn Lys Arg Pro Ser Gly Ile Pro Asp Arg Phe Ser Gly Ser
    50                  55                  60

Lys Ser Gly Thr Ser Ala Thr Leu Gly Ile Thr Gly Leu Gln Thr Gly
65                  70                  75                  80

Asp Glu Ala Asp Tyr Tyr Cys Gly Thr Trp Asp Ser Leu Ser Ala
                85                  90                  95

Val Val Phe Gly Gly Gly Thr Lys Leu Thr Val Leu
            100                 105

<210> SEQ ID NO 14
<211> LENGTH: 109
<212> TYPE: PRT
<213> ORGANISM: Homo sapiens

<400> SEQUENCE: 14

Val Leu Thr Gln Pro Pro Ser Val Ser Gly Ala Pro Gly Gln Arg Val
1               5                   10                  15

Thr Ile Ser Cys Thr Gly Ser Ser Asn Ile Gly Ala Gly Tyr Asp
                20                  25                  30

Val His Trp Tyr Gln Gln Leu Pro Gly Thr Ala Pro Lys Leu Leu Ile
            35                  40                  45

Tyr Gly Asn Ser Asn Arg Pro Ser Gly Val Pro Asp Arg Phe Ser Gly
    50                  55                  60

Ser Lys Ser Gly Thr Ser Ala Ser Leu Ala Ile Thr Gly Leu Gln Ala
65                  70                  75                  80

Glu Asp Glu Ala Asp Tyr Tyr Cys Gln Ser Tyr Asp Ser Ser Leu Ser
                85                  90                  95

Gly Val Val Phe Gly Gly Gly Thr Lys Leu Thr Val Leu
            100                 105

<210> SEQ ID NO 15
<211> LENGTH: 109
<212> TYPE: PRT
<213> ORGANISM: Homo sapiens

<400> SEQUENCE: 15
```

```
Ala Leu Thr Gln Pro Ala Ser Val Ser Gly Ser Pro Gly Gln Ser Ile
  1               5                  10                  15

Thr Ile Ser Cys Thr Gly Thr Ser Ser Asp Val Gly Gly Tyr Asn Tyr
                 20                  25                  30

Val Ser Trp Tyr Gln Gln His Pro Gly Lys Ala Pro Lys Leu Met Ile
             35                  40                  45

Tyr Glu Val Ser Asn Arg Pro Ser Gly Val Ser Asn Arg Phe Ser Gly
 50                  55                  60

Ser Lys Ser Gly Asn Thr Ala Ser Leu Thr Ile Ser Gly Leu Gln Ala
 65                  70                  75                  80

Glu Asp Glu Ala Asp Tyr Tyr Cys Ser Ser Tyr Thr Ser Ser Ser Thr
                 85                  90                  95

Leu Val Val Phe Gly Gly Gly Thr Lys Leu Thr Val Leu
                100                 105
```

<210> SEQ ID NO 16
<211> LENGTH: 104
<212> TYPE: PRT
<213> ORGANISM: Homo sapiens

<400> SEQUENCE: 16

```
Glu Leu Thr Gln Asp Pro Ala Val Ser Val Ala Leu Gly Gln Thr Val
  1               5                  10                  15

Arg Ile Thr Cys Gln Gly Asp Ser Leu Arg Ser Tyr Tyr Ala Ser Trp
                 20                  25                  30

Tyr Gln Gln Lys Pro Gly Gln Ala Pro Val Leu Val Ile Tyr Gly Lys
             35                  40                  45

Asn Asn Arg Pro Ser Gly Ile Pro Asp Arg Phe Ser Gly Ser Ser Ser
 50                  55                  60

Gly Asn Thr Ala Ser Leu Thr Ile Thr Gly Ala Gln Ala Glu Asp Glu
 65                  70                  75                  80

Ala Asp Tyr Tyr Cys Asn Ser Arg Asp Ser Ser Gly Asn His Phe Gly
                 85                  90                  95

Gly Gly Thr Lys Leu Thr Val Leu
                100
```

<210> SEQ ID NO 17
<211> LENGTH: 106
<212> TYPE: PRT
<213> ORGANISM: Homo sapiens

<400> SEQUENCE: 17

```
Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Ser Ser Pro
             35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
                100                 105
```

<210> SEQ ID NO 18
<211> LENGTH: 227
<212> TYPE: PRT
<213> ORGANISM: Homo sapiens

<400> SEQUENCE: 18

Gln Val Gln Leu Val Gln Ser Gly Ala Glu Val Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 19
<211> LENGTH: 215
<212> TYPE: PRT
<213> ORGANISM: Homo sapiens

<400> SEQUENCE: 19

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

```
Leu Thr Phe Gly Gln Gly Thr Lys Val Glu Ile Lys Arg Thr Val Ala
            100                 105                 110

Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                    165                 170                 175

Ser Ser Thr Leu Thr Leu Ser Lys Ala Asp Tyr Glu Lys His Lys Val
                    180                 185                 190

Tyr Ala Cys Glu Val Thr His Gln Gly Leu Ser Leu Pro Val Thr Lys
            195                 200                 205

Ser Phe Asn Arg Gly Glu Cys
        210                 215

<210> SEQ ID NO 20
<211> LENGTH: 227
<212> TYPE: PRT
<213> ORGANISM: Homo sapiens

<400> SEQUENCE: 20

Gln Val Gln Leu Val Gln Ser Gly Ala Glu Val Lys Lys Pro Gly Ser
 1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr
225
```

```
<210> SEQ ID NO 21
<211> LENGTH: 214
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210

<210> SEQ ID NO 22
<211> LENGTH: 227
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 23
<211> LENGTH: 214
<212> TYPE: PRT
<213> ORGANISM: Homo sapiens

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210

<210> SEQ ID NO 24
<211> LENGTH: 227
<212> TYPE: PRT
<213> ORGANISM: Homo sapiens
```

<400> SEQUENCE: 24

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gln Leu Trp Gly Tyr Tyr Ala Leu Glu Ile Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr
225

<210> SEQ ID NO 25
<211> LENGTH: 219
<212> TYPE: PRT
<213> ORGANISM: Homo sapiens

<400> SEQUENCE: 25

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Leu Leu Ile Tyr Trp Ala Ser Thr Arg Glu Ser Gly Val Pro
    50                  55                  60
Asp Arg Phe Ser Gly Ser Gly Ser Gly Thr Asp Phe Thr Leu Thr Ile
65                  70                  75                  80
Ser Ser Leu Gln Ala Glu Asp Val Ala Val Tyr Tyr Cys Gln Gln Tyr
                85                  90                  95
Tyr Ser Thr Pro Leu Thr Phe Gly Gln Gly Thr Lys Val Glu Ile Lys
            100                 105                 110
Arg Thr Val Ala Ala Pro Ser Val Phe Ile Phe Pro Pro Ser Asp Glu
        115                 120                 125

```
Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Leu
            195                 200                 205

Pro Val Thr Lys Ser Phe Asn Arg Gly Glu Cys
    210                 215

<210> SEQ ID NO 26
<211> LENGTH: 227
<212> TYPE: PRT
<213> ORGANISM: Homo sapiens

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr
225

<210> SEQ ID NO 27
<211> LENGTH: 215
<212> TYPE: PRT
<213> ORGANISM: Homo sapiens

<400> SEQUENCE: 27
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Leu Pro Val Thr Lys
        195                 200                 205

Ser Phe Asn Arg Gly Glu Cys
    210                 215

<210> SEQ ID NO 28
<211> LENGTH: 227
<212> TYPE: PRT
<213> ORGANISM: Homo sapiens

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr
225

<210> SEQ ID NO 29
<211> LENGTH: 214
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210

<210> SEQ ID NO 30
<211> LENGTH: 227
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr
225

<210> SEQ ID NO 31
<211> LENGTH: 214
<212> TYPE: PRT
<213> ORGANISM: Homo sapiens

<400> SEQUENCE: 31

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210

<210> SEQ ID NO 32
<211> LENGTH: 227
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 33
<211> LENGTH: 219
<212> TYPE: PRT
<213> ORGANISM: Homo sapiens

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
```

```
                35                  40                  45
Pro Pro Leu Leu Ile Tyr Trp Ala Ser Thr Arg Glu Ser Gly Val Pro
 50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Gln Gln Tyr
                 85                  90                  95

Tyr Ser Thr Pro Leu Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Leu
                195                 200                 205

Pro Val Thr Lys Ser Phe Asn Arg Gly Glu Cys
                210                 215
```

<210> SEQ ID NO 34
<211> LENGTH: 225
<212> TYPE: PRT
<213> ORGANISM: Homo sapiens

<400> SEQUENCE: 34

```
Val Gln Leu Val Glu Thr Gly Gly Gly Leu Ile Gln Pro Gly Gly Ser
 1                   5                  10                  15

Leu Arg Leu Ser Cys Ala Ala Ser Gly Phe Thr Val Ser Ser Asn Tyr
                 20                  25                  30

Met Ser Trp Val Arg Gln Ala Pro Gly Lys Gly Leu Glu Trp Val Ser
                 35                  40                  45

Val Ile Tyr Ser Gly Gly Ser Thr Tyr Tyr Ala Asp Ser Val Lys Gly
                 50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Gln Leu Trp Gly Tyr Tyr Ala Leu Glu Ile Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
                130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190
```

```
Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr
225

<210> SEQ ID NO 35
<211> LENGTH: 215
<212> TYPE: PRT
<213> ORGANISM: Homo sapiens

<400> SEQUENCE: 35

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Leu Pro Val Thr Lys
        195                 200                 205

Ser Phe Asn Arg Gly Glu Cys
    210                 215

<210> SEQ ID NO 36
<211> LENGTH: 225
<212> TYPE: PRT
<213> ORGANISM: Homo sapiens

<400> SEQUENCE: 36

Val Gln Leu Val Glu Thr Gly Gly Gly Leu Ile Gln Pro Gly Gly Ser
1               5                   10                  15

Leu Arg Leu Ser Cys Ala Ala Ser Gly Phe Thr Val Ser Ser Asn Tyr
            20                  25                  30

Met Ser Trp Val Arg Gln Ala Pro Gly Lys Gly Leu Glu Trp Val Ser
        35                  40                  45

Val Ile Tyr Ser Gly Gly Ser Thr Tyr Tyr Ala Asp Ser Val Lys Gly
    50                  55                  60
```

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gln Leu Trp Gly Tyr Tyr Ala Leu Glu Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr
225

<210> SEQ ID NO 37
<211> LENGTH: 214
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

```
Phe Asn Arg Gly Glu Cys
    210

<210> SEQ ID NO 38
<211> LENGTH: 225
<212> TYPE: PRT
<213> ORGANISM: Homo sapiens

<400> SEQUENCE: 38

Val Gln Leu Val Glu Thr Gly Gly Gly Leu Ile Gln Pro Gly Gly Ser
  1               5                  10                  15

Leu Arg Leu Ser Cys Ala Ala Ser Gly Phe Thr Val Ser Ser Asn Tyr
             20                  25                  30

Met Ser Trp Val Arg Gln Ala Pro Gly Lys Gly Leu Glu Trp Val Ser
         35                  40                  45

Val Ile Tyr Ser Gly Gly Ser Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Gln Leu Trp Gly Tyr Tyr Ala Leu Glu Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr
225

<210> SEQ ID NO 39
<211> LENGTH: 214
<212> TYPE: PRT
<213> ORGANISM: Homo sapiens

<400> SEQUENCE: 39

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80
```

```
Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210

<210> SEQ ID NO 40
<211> LENGTH: 225
<212> TYPE: PRT
<213> ORGANISM: Homo sapiens

<400> SEQUENCE: 40

Val Gln Leu Val Glu Thr Gly Gly Gly Leu Ile Gln Pro Gly Gly Ser
  1               5                  10                  15

Leu Arg Leu Ser Cys Ala Ala Ser Gly Phe Thr Val Ser Ser Asn Tyr
             20                  25                  30

Met Ser Trp Val Arg Gln Ala Pro Gly Lys Gly Leu Glu Trp Val Ser
         35                  40                  45

Val Ile Tyr Ser Gly Gly Ser Thr Tyr Tyr Ala Asp Ser Val Lys Gly
     50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Arg
                 85                  90                  95

Gln Leu Trp Gly Tyr Tyr Ala Leu Glu Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr
```

```
<210> SEQ ID NO 41
<211> LENGTH: 219
<212> TYPE: PRT
<213> ORGANISM: Homo sapiens

<400> SEQUENCE: 41

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Lys Pro Gly Gln
        35                  40                  45

Pro Pro Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Thr Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Leu
        195                 200                 205

Pro Val Thr Lys Ser Phe Asn Arg Gly Glu Cys
    210                 215

<210> SEQ ID NO 42
<211> LENGTH: 227
<212> TYPE: PRT
<213> ORGANISM: Homo sapiens

<400> SEQUENCE: 42

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Leu Trp Gly Tyr Tyr Ala Leu Glu Ile Trp Gly Gln Gly
```

```
              100                 105                 110
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 43
<211> LENGTH: 215
<212> TYPE: PRT
<213> ORGANISM: Homo sapiens

<400> SEQUENCE: 43

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Leu Pro Val Thr Lys
        195                 200                 205

Ser Phe Asn Arg Gly Glu Cys
    210                 215

<210> SEQ ID NO 44
<211> LENGTH: 227
```

<212> TYPE: PRT
<213> ORGANISM: Homo sapiens

<400> SEQUENCE: 44

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225
```

<210> SEQ ID NO 45
<211> LENGTH: 214
<212> TYPE: PRT
<213> ORGANISM: Homo sapiens

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210

<210> SEQ ID NO 46
<211> LENGTH: 227
<212> TYPE: PRT
<213> ORGANISM: Homo sapiens

<400> SEQUENCE: 46

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 47
<211> LENGTH: 214
<212> TYPE: PRT
<213> ORGANISM: Homo sapiens
```

<400> SEQUENCE: 47

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Leu
             85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Leu Pro Val Thr Lys Ser
    195                 200                 205

Phe Asn Arg Gly Glu Cys
    210
```

<210> SEQ ID NO 48
<211> LENGTH: 227
<212> TYPE: PRT
<213> ORGANISM: Homo sapiens

<400> SEQUENCE: 48

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
         35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
             85                  90                  95

Ala Arg Gln Leu Trp Gly Tyr Tyr Ala Leu Glu Ile Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr
225

<210> SEQ ID NO 49
<211> LENGTH: 219
<212> TYPE: PRT
<213> ORGANISM: Homo sapiens

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Thr Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Leu
        195                 200                 205

Pro Val Thr Lys Ser Phe Asn Arg Gly Glu Cys
    210                 215

<210> SEQ ID NO 50
<211> LENGTH: 28
<212> TYPE: DNA
<213> ORGANISM: Homo sapiens

<400> SEQUENCE: 50
cgtacgttta atttccactt tggtgccc                                    28
```

<210> SEQ ID NO 51
<211> LENGTH: 46
<212> TYPE: DNA
<213> ORGANISM: Homo sapiens

<400> SEQUENCE: 51
taaccgggtc tagaccccct gaaaacaggg ggtctagacc cggtta        46

<210> SEQ ID NO 52
<211> LENGTH: 48
<212> TYPE: DNA
<213> ORGANISM: Homo sapiens

<400> SEQUENCE: 52
agggttaggc gcgcctggtc gcaaaagcga ccaggcgcgc ctaaccca      48

<210> SEQ ID NO 53
<211> LENGTH: 20
<212> TYPE: DNA
<213> ORGANISM: Homo sapiens

<400> SEQUENCE: 53
tggtgctttt gctgctcggc                                     20

<210> SEQ ID NO 54
<211> LENGTH: 20
<212> TYPE: DNA
<213> ORGANISM: Homo sapiens

<400> SEQUENCE: 54
ctggtttgtt attactcgcg                                     20

<210> SEQ ID NO 55
<211> LENGTH: 231
<212> TYPE: PRT
<213> ORGANISM: Homo sapiens

<400> SEQUENCE: 55

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Asn Gly Asn Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Gly Met Arg Val Gln Thr Tyr Tyr Phe Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe

```
                    165                 170                 175
Pro Ala Val Leu Gln Ser Ser Gly Leu Tyr Ser Leu Ser Val Val
            180                 185                 190

Thr Val Pro Ser Ser Leu Gly Thr Gln Thr Tyr Ile Cys Asn Val
            195                 200                 205

Asn His Lys Pro Ser Asn Thr Lys Val Asp Lys Val Glu Pro Lys
            210                 215                 220

Ser Cys Asp Lys Thr His Thr
225                 230
```

<210> SEQ ID NO 56
<211> LENGTH: 219
<212> TYPE: PRT
<213> ORGANISM: Homo sapiens

<400> SEQUENCE: 56

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Thr Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Leu
        195                 200                 205

Pro Val Thr Lys Ser Phe Asn Arg Gly Glu Cys
    210                 215
```

<210> SEQ ID NO 57
<211> LENGTH: 230
<212> TYPE: PRT
<213> ORGANISM: Homo sapiens

<400> SEQUENCE: 57

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
```

```
            35                  40                  45
Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Cys Val Ser Pro Ala Trp Asp Gln Cys Phe Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr
225                 230

<210> SEQ ID NO 58
<211> LENGTH: 219
<212> TYPE: PRT
<213> ORGANISM: Homo sapiens

<400> SEQUENCE: 58

Asp Ile Val Met Thr Gln Ser Pro Asp Ser Leu Ala Val Ser Leu Gly
 1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Leu Leu Ile Tyr Trp Ala Ser Thr Arg Glu Ser Gly Val Pro
 50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Gln Gln Tyr
                 85                  90                  95

Tyr Ser Thr Pro Leu Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Leu
        195                 200                 205

Pro Val Thr Lys Ser Phe Asn Arg Gly Glu Cys
    210                 215

<210> SEQ ID NO 59
<211> LENGTH: 229
<212> TYPE: PRT
<213> ORGANISM: Homo sapiens

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ile Ile Gly Ile Asn Leu Val Val Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr
225

<210> SEQ ID NO 60
<211> LENGTH: 219
<212> TYPE: PRT
<213> ORGANISM: Homo sapiens

<400> SEQUENCE: 60

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

```
Pro Pro Leu Leu Ile Tyr Trp Ala Ser Thr Arg Glu Ser Gly Val Pro
    50                  55                  60
Asp Arg Phe Ser Gly Ser Gly Ser Gly Thr Asp Phe Thr Leu Thr Ile
65                  70                  75                  80
Ser Ser Leu Gln Ala Glu Asp Val Ala Val Tyr Tyr Cys Gln Gln Tyr
                85                  90                  95
Tyr Ser Thr Pro Leu Thr Phe Gly Gln Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Leu
        195                 200                 205
Pro Val Thr Lys Ser Phe Asn Arg Gly Glu Cys
210                 215

<210> SEQ ID NO 61
<211> LENGTH: 230
<212> TYPE: PRT
<213> ORGANISM: Homo sapiens

<400> SEQUENCE: 61

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ile Arg Trp Gly Gly Trp Phe Arg Gly Tyr Leu Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
```

His Lys Pro Ser Asn Thr Lys Val Asp Lys Lys Val Glu Pro Lys Ser
    210                 215                 220

Cys Asp Lys Thr His Thr
225                 230

<210> SEQ ID NO 62
<211> LENGTH: 215
<212> TYPE: PRT
<213> ORGANISM: Homo sapiens

<400> SEQUENCE: 62

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Leu Pro Val Thr Lys
        195                 200                 205

Ser Phe Asn Arg Gly Glu Cys
    210                 215

<210> SEQ ID NO 63
<211> LENGTH: 231
<212> TYPE: PRT
<213> ORGANISM: Homo sapiens

<400> SEQUENCE: 63

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Asp Phe Gly Val Tyr Thr Trp Leu Gly Gln Thr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr
225                 230

<210> SEQ ID NO 64
<211> LENGTH: 215
<212> TYPE: PRT
<213> ORGANISM: Homo sapiens

<400> SEQUENCE: 64

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Leu Pro Val Thr Lys
        195                 200                 205

Ser Phe Asn Arg Gly Glu Cys
```

<210> SEQ ID NO 65
<211> LENGTH: 229
<212> TYPE: PRT
<213> ORGANISM: Homo sapiens

<400> SEQUENCE: 65

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ile Ile Gly Thr Ile Thr Tyr Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr
225

<210> SEQ ID NO 66
<211> LENGTH: 219
<212> TYPE: PRT
<213> ORGANISM: Homo sapiens

<400> SEQUENCE: 66

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr

```
                    85                  90                  95
Tyr Ser Thr Pro Leu Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Leu
            195                 200                 205

Pro Val Thr Lys Ser Phe Asn Arg Gly Glu Cys
        210                 215

<210> SEQ ID NO 67
<211> LENGTH: 226
<212> TYPE: PRT
<213> ORGANISM: Homo sapiens

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Ile Pro Tyr Asn Gly Asn Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Thr Pro Val Arg Asp Leu Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr
225
```

<210> SEQ ID NO 68
<211> LENGTH: 219
<212> TYPE: PRT
<213> ORGANISM: Homo sapiens

<400> SEQUENCE: 68

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Leu Leu Ile Tyr Trp Ala Ser Thr Arg Glu Ser Gly Val Pro
     50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Gln Gln Tyr
                 85                  90                  95

Tyr Ser Thr Pro Leu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Leu
        195                 200                 205

Pro Val Thr Lys Ser Phe Asn Arg Gly Glu Cys
    210                 215
```

<210> SEQ ID NO 69
<211> LENGTH: 231
<212> TYPE: PRT
<213> ORGANISM: Homo sapiens

<400> SEQUENCE: 69

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Gly Gly Glu Val Asp Trp Glu Tyr Tyr Leu Asp Tyr
            100                 105                 110
```

```
Trp Gly Gln Gly Thr Leu Val Thr Val Ser Ser Ala Ser Thr Lys Gly
            115                 120                 125
Pro Ser Val Phe Pro Leu Ala Pro Ser Ser Lys Ser Thr Ser Gly Gly
        130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
210                 215                 220
Ser Cys Asp Lys Thr His Thr
225                 230

<210> SEQ ID NO 70
<211> LENGTH: 219
<212> TYPE: PRT
<213> ORGANISM: Homo sapiens

<400> SEQUENCE: 70

Asp Ile Val Met Thr Gln Ser Pro Asp Ser Leu Ala Val Ser Leu Gly
  1               5                  10                  15
Glu Arg Ala Thr Ile Asn Cys Lys Ser Ser Gln Ser Val Leu Tyr Ser
             20                  25                  30
Ser Asn Asn Lys Asn Tyr Leu Ala Trp Tyr Gln Gln Lys Pro Gly Gln
         35                  40                  45
Pro Pro Leu Leu Ile Tyr Trp Ala Ser Thr Arg Glu Ser Gly Val Pro
     50                  55                  60
Asp Arg Phe Ser Gly Ser Gly Ser Gly Thr Asp Phe Thr Leu Thr Ile
 65                  70                  75                  80
Ser Ser Leu Gln Ala Glu Asp Val Ala Val Tyr Tyr Cys Gln Gln Tyr
                 85                  90                  95
Tyr Ser Thr Pro Leu Thr Phe Gly Gln Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Leu
        195                 200                 205
Pro Val Thr Lys Ser Phe Asn Arg Gly Glu Cys
    210                 215

<210> SEQ ID NO 71
<211> LENGTH: 229
<212> TYPE: PRT
<213> ORGANISM: Homo sapiens
```

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Trp Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Pro Phe Arg Tyr Trp Pro Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr
225

<210> SEQ ID NO 72
<211> LENGTH: 214
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210
```

<210> SEQ ID NO 73
<211> LENGTH: 226
<212> TYPE: PRT
<213> ORGANISM: Homo sapiens

<400> SEQUENCE: 73

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn His Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ile Gly Ala Asp Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr
225
```

<210> SEQ ID NO 74
<211> LENGTH: 214
<212> TYPE: PRT
<213> ORGANISM: Homo sapiens

<400> SEQUENCE: 74

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ala Ser Trp
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Gly Trp Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Leu Pro Val Thr Lys Ser
        195                 200                 205

Phe Asn Arg Gly Glu Cys
    210

<210> SEQ ID NO 75
<211> LENGTH: 226
<212> TYPE: PRT
<213> ORGANISM: Homo sapiens

<400> SEQUENCE: 75

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Gly Ser Ser Val Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
```

```
                145                 150                 155                 160
Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
                    180                 185                 190

Ser Leu Gly Thr Gln Thr Tyr Ile Cys Asn Val Asn His Lys Pro Ser
                    195                 200                 205

Asn Thr Lys Val Asp Lys Lys Val Glu Pro Lys Ser Cys Asp Lys Thr
                    210                 215                 220

His Thr
225

<210> SEQ ID NO 76
<211> LENGTH: 214
<212> TYPE: PRT
<213> ORGANISM: Homo sapiens

<400> SEQUENCE: 76

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ala Asp Asp
                20                  25                  30

Leu Ala Trp Tyr Gln Gln Lys Pro Gly Gln Ala Pro Arg Leu Leu Ile
            35                  40                  45

Tyr Tyr Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Gly Ala Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Leu Pro Val Thr Lys Ser
            195                 200                 205

Phe Asn Arg Gly Glu Cys
        210

<210> SEQ ID NO 77
<211> LENGTH: 225
<212> TYPE: PRT
<213> ORGANISM: Homo sapiens

<400> SEQUENCE: 77

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
```

```
                 20                  25                  30
Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Tyr Arg Ser Phe Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr
225

<210> SEQ ID NO 78
<211> LENGTH: 214
<212> TYPE: PRT
<213> ORGANISM: Homo sapiens

<400> SEQUENCE: 78

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Arg Ser Tyr
             20                  25                  30

Leu Ala Trp Tyr Gln Gln Lys Pro Gly Gln Ala Pro Arg Leu Leu Ile
         35                  40                  45

Tyr Ala Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Gly Trp Pro Ile
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Leu Pro Val Thr Lys Ser
        195                 200                 205
Phe Asn Arg Gly Glu Cys
    210

<210> SEQ ID NO 79
<211> LENGTH: 42
<212> TYPE: PRT
<213> ORGANISM: Homo sapiens

<400> SEQUENCE: 79

Ala Pro Thr Glu Cys Ser Thr Ser Gly Gly Gly Ser Met Ser Val
1               5                   10                  15
Leu Val Tyr Ser Phe Ala Ser Phe Val Leu Gly Trp Cys Leu Arg Ser
                20                  25                  30
Gly Ile Thr Tyr Phe Thr Arg Leu Met Glu
            35                  40
```

GENERATION OF HUMAN *DE NOVO* PIX PHAGE DISPLAY LIBRARIES

This application is a continuation-in-part of PCT/US2008/084255 filed on Nov. 21, 2008, which claims priority to U.S. Provisional Application Ser. No. 61/014,786, filed on Dec. 19, 2007.

BACKGROUND

The invention relates to compositions and methods for generating and using pIX phage display libraries for producing antibodies or antibody fragments.

Filamentous phage display using pIII and pVIII as fusion partners in phage or phagemid systems have been used as a technology for protein engineering, notably for de novo antibody isolation and affinity maturation. Human-like Fab sequences can be generated from known antibody template sequences and random or mutangenized complementarity determining regions (CDR) or antigen binding regions, such as heavy chain CDR3 (H3). Such sequences can be generated and isolated from phage libraries displaying variations of antibody fragment sequences via panning against an antigen or other target of interest without immunization. Previously used human de novo antibody libraries have been created synthetically or by molecular cloning of IgG genes from naive source(s) or by combinations of both methods. In a synthetic library, antibody DNA sequences including variable heavy chain and light chain framework sequences, and the CDR regions, are designed and synthesized based on 1) a defined IgG gene; 2) a specific Ig germline gene; 3) consensus sequences from families of the Ig germline genes; and/or 4) PCR-derived IgG fragments from natural sources. Libraries may also be created by combinatorial cloning of IgG DNA derived from human tissues, e.g. bone marrow and peripheral blood cells. Such libraries have been used for providing Fab antibody fragments (i.e., the antigen-binding fragment of an immunoglobulin molecule, comprising both a light chain and part of a heavy chain) and for running successive rounds of panning and maturation or modification to find Fab antibody fragments that have desired properties such as high affinity target binding or the ability to modulate the biological activity of a selected target protein.

Human-like Fabs that bind target proteins have been isolated from phage display pIII or pVIII de novo libraries. Although successful at isolating Fabs that bind to specific targets, such phage display library approaches often suffer from the problem of having to repeat the process of library generation, panning for Fabs that bind to a target of interest, and maturing the Fabs one or more times to isolate Fab antibodies having the desired characteristics. Some phage libraries also suffer from the problem that they do not fully encompass or mimic the full range of human immune diversity, including the contribution of $V_H/V_L$ paring, topology features of different germline families related to antigen recognition, the position and extent of amino acid variation, and the relative abundance of antibodies derived from different human germline genes. Deviation of synthetic antibodies from the natural repertoire may increase the risk of unfavorable biochemical properties and of immunogenicity if used as therapeutics in humans.

Counter to prior conclusions (See e.g., Endemann and Model, *J. Mol. Biol.*, 250: 496-506, 1995), the filamentous phage proteins pVII and pIX were found to localize on the phage surface in an orientation suitable for protein and peptide display (Gao et al., *Proc Natl Acad Sci USA*, 96: 6025-6030, 1999). Subsequently, the pIX protein was utilized for display of a single chain antibody library (Gao et al., *Proc Natl Acad Sci USA*, 99: 12612-12616, 2002). However, this approach was not successful for construction and display of Fab libraries.

There is a need for synthetic antibody libraries and methods that simultaneously deliver the elements of human therapeutic antibodies of high affinity and activity, high productivity, good solution properties, and a propensity of low immune response when administered in humans. There is a further need to increase the efficiency of antibody isolation from synthetic libraries, relative to current methods, to reduce the resource costs of antibody discovery and accelerate delivery of antibodies for biological evaluation. The libraries and methods of this invention meet these needs by coupling comprehensive design, assembly technologies, and phage pIX Fab display.

SUMMARY OF THE INVENTION

The subject matter disclosed and claimed herein is directed to improved and new pIX phage display de novo library generation methods and components, such as, but not limited to, one or more of (i) designed and displayed antibody Fab de novo libraries fused to the pIX phage proteins; (ii) the use of a phage surface protein different from the widely used pIII and pVIII of M13 phage; (iii) the use of a small array of germline $V_H$ and $V_L$ genes representing the sequence and structure of the human antibody repertoire; (iv) use of such components as the library scaffold to provide improved combinatorial diversities in the complementarity determining regions of the $V_H$ and $V_L$ regions; (v) antibody selection processes that allow systematic examination of the effect of the designed sequences and structural topographies for antigen recognition; and (vi) a streamlined in line affinity maturation process as a part of the library selection. This new system of library design, selection, optimization and maturation of individual or groups of libraries provides a reproducible and reliable system for successful antibody de novo discovery and also facilitates understanding of the structure-function relation of antibody-antigen interactions.

pIX mediated phage display can be used for generating high affinity Fab libraries using mutagenesis or other diversity producing techniques, optionally with in-line maturation, to provide an efficient and fast platform for Fab and antibody fragment generation and selection of therapeutic antibodies. According to the present invention, antibody heavy or light chain Fab regions fused to pIX engage corresponding soluble light or heavy chain fragments in a dynamic interaction on the phage surface to display a functional antibody fragment, a representative heterodimeric motif. The display on phage of antibody heavy and light chain Fab regions is therefore a suitable and preferred method for display and assay of diverse libraries of combinatorial heterodimeric arrays in which members can function as dimeric artificial antibody species and allows for selection of novel or desired biological activities.

In a preferred embodiment, a filamentous phage encapsulates a genome which encodes a fusion protein coupled with a secreted soluble binding partner protein, where the first fusion protein comprises a first exogenous polypeptide fused to pIX.

The filamentous phage may further contain fusion protein(s) displayed on the surface of the phage particle, as described in the Examples. Thus, where there is a fusion protein, and a secreted binding partner protein, the phage can display a heterodimeric protein in a functional manner such that the first and second exogenous polypeptides can interact as a heterodimer to form a functional two-chain protein complex on the phage surface. Where an expressed heterodimeric protein has the capacity to bind ligand, it is alternatively referred to herein as a ligand-binding heterodimeric receptor. The heterodimeric receptor in a preferred embodiment is an epitope-binding complex. That is, a complex of first and second polypeptides capable of binding an epitope. Preferably, the first and second polypeptides are antibody heavy chain and light chain polypeptides. In particular, a preferred embodiment utilizes Fd and Lc to form a Fab complex. Other heterodimeric protein complexes include a catalytic Fab, and N-terminal, C-terminal or insertion fusion constructs to the Fd or Lc wherein the Fab serves as a scaffold for formation of a heterodimeric complex.

In a fusion protein present on a phage of this invention, the "fusion" between the exogenous polypeptide and the filamentous phage pIX protein may comprise a typical amide linkage, or may comprise a linker polypeptide (i.e., a "linker") as described in the Examples. Any of a variety of linkers may be used which are typically a stretch of about 5 to 50 amino acids in length. Particularly preferred linkers provide a high degree of mobility to the fusion protein at the point of the linker.

One distinguishing factor of the display methods described herein is that the instant methods employ representative human germline and structure sequences as the library scaffolds, and CDR sequences that mimic the natural CDR amino acid distribution. Moreover, the sequences employed in the instant methods comprehensively cover the human immune repertoire and the library antibodies have high sequence identity to the natural derived human antibodies. The comprehensive coverage of the human immune repertoire increases the chance of de novo antibody discovery compared to libraries built on a single germline or IgG gene scaffold such as those reported in literature. The separately constructed sub-libraries, each carrying a unique scaffold ($V_H/V_L$ pair) and/or H-CDR3 lengths, maximize the probability of identifying a unique antibody and provide a mechanism to systematically examine antibody-antigen binding and study the structure-function relationships. Additionally, the integrated affinity maturation process reduces the time required to discover diverse and high affinity antibodies.

The methods disclosed are preferable over earlier reports using pIX display for generation of Fabs or Fab-based antibody molecules, including monoclonal antibodies for a number of reasons. For example, earlier work describes display of scFv libraries by pIX (Gao, C. et al. Proc Natl Acad Sci USA 99, 12612-12616, 2002); but the transfer of properties from scFv to full antibodies, or even to Fabs, is less predictable than transfer from Fabs. In addition, scFv often have other undesirable biochemical properties such as poor solubility and low stability. Other reports involve the parallel display of $V_H$ and $V_L$ domains as fusion proteins to pVII and pIX proteins, respectively, or the converse (Gao, C. et al. Proc Natl Acad Sci USA. 96, 6025-6030 (1999). This approach is less facile than Fab display and suffers the same disadvantages as the scFv format noted above. In addition, several technical features were combined in a novel manner to enable facile construction of Fab display libraries and the in-line maturation process. The processes involve the use of megaprimers with the well-known Kunkel's methods to efficiently introduce diversity into multiple CDR regions of scaffold templates and the use of loop structures with a unique restriction endonuclease site to minimize parental contamination for library construction. Furthermore, these technical features are combined with a comprehensive library design that incorporates representative human germline and structure sequences as the library scaffolds and CDR sequences that reflect the natural amino acid distribution of antibodies to comprehensively cover the human immune repertoire. The separate assembly of framework libraries enables varied library formats with separate or pools of HC and LC combinations to maximize the discovery of multiple unique antibodies to a given target. The integrated ability to directly introduce diversity into recovered phagemids after any step of selection enables selection of antibodies of higher affinity and selectivity than from single step library systems.

The subject matter described herein also includes a combinatorial phage display format for construction of highly diverse heterodimeric polypeptide arrays. In a particular embodiment, a filamentous phage particle encapsulating a genome encoding a fusion polypeptide is used, wherein the fusion polypeptide comprises an exogenous antibody Fd or light chain polypeptide fused to the amino terminus of a filamentous phage pIX protein. Preferably, the phage particle comprises the expressed fusion protein on the surface of the phage particle.

In a preferred embodiment, the phage genome is a phagemid that further encodes a second secreted polypeptide, wherein the second secreted polypeptide is an antibody light chain or heavy chain Fd fragment. In this embodiment, the antibody Fd polypeptide fused to pIX can associate with the secreted antibody light chain to form a heterodimeric Fab protein complex. In a second preferred embodiment, the antibody light chain polypeptide fused to pIX can associate with the secreted antibody Fd chain to form a heterodimeric Fab protein complex.

Another embodiment is a vector for expressing a Fab fusion protein on the surface of a filamentous phage comprising a cassette for expressing the Fab fusion protein. The cassette includes upstream and downstream translatable DNA sequences operatively linked via a sequence of nucleotides adapted for directional ligation of an insert DNA, i.e., a polylinker, where the upstream sequence encodes a prokaryotic secretion signal, and the downstream sequence encodes a pIX filamentous phage protein. The translatable Fd, or light chain DNA sequences are operatively linked to a set of DNA expression signals for expression of the translatable DNA sequences as portions of the fusion polypeptide. In a preferred embodiment, the vector further comprises a second cassette for expressing a Fd, or light chain protein chain as a secreted protein, wherein the second cassette comprises the structure of the first cassette with the proviso that the second cassette does not encode a pIX fusion protein. The vector is used as a phagemid, or phage genome, to express heterodimeric Fab protein complexes on the surface of the phage particle in which one of the two exogenous polypeptides of the heterodimer is anchored on the phage particle by the fusion to the pIX phage protein.

Another embodiment is a library of phage particles according to the present invention, i.e., a combinatorial library, in which representative particles in the library each display a different fusion protein. Where the particle displays a heterodimeric protein complex, the library comprises a combinatorial library of heterodimers, such as antibodies in the form of a library of Fab molecules. Preferred libraries have a combinatorial diversity of at least about $10^3$ and as high as $10^{13}$, or any range or value therein, of different species of fusion protein.

Further described are a variety of methods for producing a combinatorial library of phage, including cloning repertoires of genes encoding an exogenous polypeptide into a vector of the present invention, modifying the structure of the exogenous polypeptides in a library by mutagenesis, random combination of populations of fusion and non-fusion protein libraries, and target/affinity selection ("panning") to alter the diversity of a library, and the like.

The present invention provides for the display and selection of mutant dimeric proteins and combinatorial libraries in which members comprise heterodimeric arrays. Using this technology, the native immunoglobulin structure, in a heterodimeric Fab format shown herein, can be modified in different ways and screened for specificity and activity. For example, by combinatorial alteration of framework regions (FRs) or other manipulations to reorganize and miniaturize the antibody structure by processes coined "CDR shuffling" formation, antibody-like secondary structures will emerge that contain new paratopes or entirely different structural elements. Selection for binding and/or catalysis against the natural antigen and/or substrate as well as some related compounds will be used to screen the libraries of heterodimeric proteins.

Furthermore, sequence randomizations to form libraries and chain-shuffling protocols to form hybrid species can lead to subsets of novel proteins. For instance, the display and modification of arrays of zinc-finger domains in homodimeric or heterodimeric form produces structures that possess specific DNA interactions. In addition, entirely new constructs are possible via the insertion of a desired encoding fragment within a preformed scaffold such as a Fab antibody chain. Possible insertions include an enzyme signature sequence or a repressor binding protein.

The design of proteins with improved or novel functions has a variety of medical, industrial, environmental, and research applications. Following the development of combinatorial antibody libraries, a next step is the evolution toward artificial antibody constructs, as well as other protein motifs in which dimeric species are functional and closely mimic native antibodies or fragments thereof.

The subject matter disclosed and claimed herein addresses these challenges by providing a phage-display format for the construction of combinatorial heterodimeric polypeptide arrays in which pIX is utilized in combination with secreted non-fusion protein partners for the display of fusion proteins that form dimeric species.

It should be understood that both the foregoing general description and the following detailed description are exemplary and explanatory only and are not restrictive of the subject matter disclosed and claimed herein.

DESCRIPTION OF THE FIGURES

FIG. 2. Amino acid sequence showing the Lc and pIX fusion. The amino acid residues APTEC (underlined bold) encode the C-terminal end of the Lc. G4S is an exemplary linker (italicized). The remainder of the downstream sequence is the peptide corresponding to pIX.

FIG. 6. Schematic of H-CDR3 design pattern.

FIG. 7. Schematic of H-CDR3 oligonucleotide design.

FIG. 8. Amino acid distribution in H-CDR3 positions for the H1-69 template. A. Distribution at 393 D positions (length 9-14). B. Distribution at 2163 N positions (length 9-14). C. Distribution at 973 Y positions in H-CDR3 (length 9-14); D. Distribution at all positions in H-CDR3 length 7 and 8 using NNS codon.

FIG. 15. Exemplary Fabs produced using pIX display.

FIG. 16. In-line maturation data for mTF and IgG clones.

FIG. 17. Sequences of the designed four $V_H$s and four $V_L$s.

FIG. 18. Sequences of BSA and lysozyme binders.

DETAILED DESCRIPTION OF THE INVENTION

Definitions & Explanation of Terminology

Figure 1:
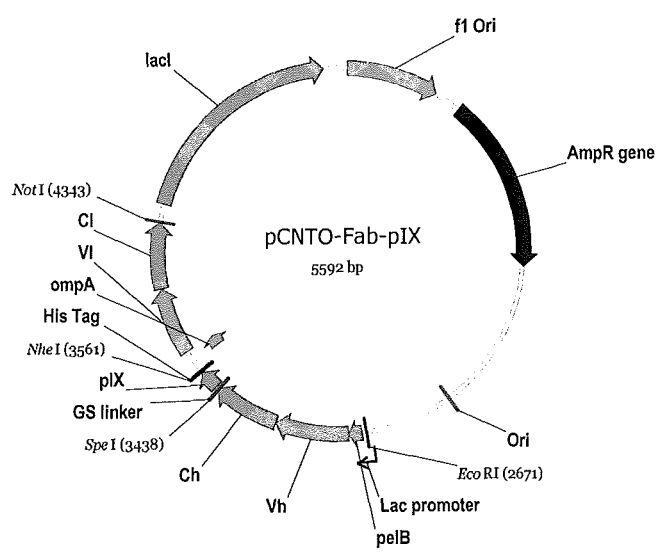
FIG. 1. Diagram of a dual phage display and Fab expression vector: pCNTO-Fab-pIX-lacI; for display of Hc linked to pIX.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are typically substantially intact immunoglobulin molecules and portions of an immunoglobulin molecule, including those portions known in the art as Fab, Fab', F(ab')$_2$ and Fv. Artificial antibodies are defined as protein motifs of large diversity that use the functional strategy of the antibody molecule, but can be generated free of in vivo constraints, including (1) sequence homology and toxicity of target antigens; (2) biological impact of the generated antibody in the host or in hybridoma cultures used to recover the antibody; and (3) screening versus selection for desired activity. The antibody molecule is a biological device for the presentation of a combinatorial array of peptide elements in three-dimensional space. One feature is that while CDRs cooperate to form a binding site, their interaction is dynamic and functional with little structural association between the CDRs themselves. In this way, the full complement of amino acid residues is available for antigen recognition at a minimum energetic cost for binding. It is proposed that the ability to control the combinatorial design of not only sequence space, but also three-dimensional space, would recapitulate and ultimately transcend the natural design of the immune repertoire.

Antigen-binding Site: An antigen-binding site is the structural portion of an antibody molecule that includes heavy and light chain-variable and hypervariable regions or portions thereof that specifically bind (immunoreact with) an antigen. The term immunoreact in its various forms means specific binding between an antigenic determinant-containing molecule and a molecule containing an antibody combining site such as a whole antibody molecule or a portion thereof.

Fusion Polypeptide: A polypeptide comprised of at least two polypeptides and a linking sequence to operatively join the two polypeptides into one continuous polypeptide. The two polypeptides linked in a fusion polypeptide are typically derived from two independent sources, and therefore a fusion polypeptide typically comprises two linked polypeptides not normally found linked in nature.

Cistron: Sequence of nucleotides in a DNA molecule coding for an amino acid residue sequence and including upstream and downstream DNA expression control elements.

Exogenous Polypeptide: A polypeptide fused to a phage protein is not normally associated with the phage protein in wild-type varieties of filamentous phage, but rather are foreign to the normal phage protein. A typical exogenous polypeptide is any polypeptide of interest, including an antibody Lc, an Fd domain, an Fc domain, an immunoglobulin heavy chain variable domain ($V_H$), an immunoglobulin light chain variable domain ($V_L$), natural or synthetic polypeptides, a single chain antibody (scFv), and the like.

Germline V-region family diversity: The human variable repertoire for heavy and light chains comprises families of related sequences that are defined by sequence homology and length. In any such family, individual members may differ primarily in sequence and length of the CDRs. These differences lead to known structural variation patterns (canonical structure) as well as germline amino acid variation at structurally similar positions that are predisposed to interact with an antigen. Choosing only a single $V_H$ and $V_L$ gene template for a library diminishes the scope of natural germline diversity that could otherwise be captured. However, choosing all $V_H$ and $V_L$ genes paralyzes the efficiency of library generation due to the high number of clones. The libraries of the current invention strike a useful balance by efficiently capturing germline diversity by (1) identifying a small number of germline $V_H$, Vk, and V-lambda that represent the dominant canonical structure groups in rearranged human antibodies (Chothia et al. *J. Mol. Biol.* 227: 799-817, 1992; Tomlinson et al. *EMBO J.* 14:4628-38, 1995; Williams et al. J. Mol. Biol. 264:220-32, 1996); and (2) incorporating the natural human germline diversity of related family members in the $V_H$ gene encoded CDRs 1 and 2, or also in CDRs 1-3 of the Vk and V-lambda regions, by combinatorial oligonucleotide mutagenesis.

$V_H$-CDR3 diversity. $V_H$-CDR3 is created by the joining of the V, D, and J segments and is accompanied by both end addition and exonucleolytic events. There are about 25 germline D region segments and this number coupled with the complex joining events and somatic mutation creates the most diverse region of antibodies. These events occur on a defined set of germline sequences and so are not random; but they are difficult to predict. However, the database of rearranged human antibody sequences now has reached sufficient size (about 5,000 $V_H$ regions) to apply statistical evaluation of both length and amino acid distribution at each position in $V_H$-CDR3. The libraries of the current invention recapitulate this natural human diversity by utilizing designed degenerate oligonucleotides to assemble this region.

Position and nature of somatic diversity. Somatic diversity is a hallmark of how human antibodies mature to high-affinity, selective binding entities. This generation and accumulation of somatic mutations is not random. The site and type of nucleotide mutation are biased by DNA sequence and mechanism but primarily mutations that provide binding and functional advantage are selected and stored, often along with neutral substitutions. While not amenable to prediction from mechanism, the database of rearranged human antibody sequences and structure-function analysis identifies positions and amino substitutions most frequently associated with recognition of antigen in CDR regions, including differentiation between protein, peptide, and small molecule antigens. The libraries of the current invention recapitulate this natural human diversity by utilizing designed degenerate oligonucleotides to incorporate substitutions into $V_H$ CDR1 and 2, or also CDRs 1-3 of the V-kappa and V-lambda light chain regions.

Germline gene usage. The human germline repertoire consists of about 30 V-kappa light, 56 V-lambda light, and 40 V-heavy chain functional genes. However, their representation in rearranged antibodies is strongly biased and this is reflected in the frequency of pairing of different light and heavy chain V-regions (de Wildt et al. *J. Mol. Biol.* 285: 895-901, 1999). The libraries of the invention capture this bias by selecting a dominant germline V-region for each of the diversity classes noted above.

Expression, biochemical, and biophysical properties. Preferred human antibodies have desired biological and binding activities, and are efficiently produced from a variety of hosts, are stable, and have good solution properties. High-frequency germline gene usage also facilitates expression in mammalian systems. In addition, antibodies recovered from libraries constructed using bacterial phage display methods of selection or screening should express well in bacterial hosts. The libraries of the invention are based on human germline derived templates that are well-expressed and purified from standard recombinant mammalian hosts (e.g. HEK 293 and CHO cells) and bacterial hosts, and have high stability and desirable solubility properties.

Maturation. The large number of positions in the V-region sequences that can impact recognition of antigen, coupled with potential variation of up to 20 different amino acids at each position preclude the practicality of including all variations in a single library. Human antibodies achieve high affinity and specificity by the progressive process of somatic mutation. The libraries of the invention are designed and ordered to permit parallel selection and targeted variation while maintaining the sequence integrity of each antibody chain such that they reflect human antibodies.

Alternative design. The above design recapitulates natural human antibodies. The modular nature of the system is amenable to incorporation of any collection of amino acids at any collection of positions.

Library assembly technologies. Preferred de novo antibody libraries are of high diversity ($>10^{10}$), amenable to alteration, easy to assemble, and have a low background of undesired sequences. These background sequences include parental template and low-targeted diversity. Coupling the following methods accelerates library assembly and leads to low background: (a) Kunkel-based single-stranded mutagenesis; (b) Palindromic loop with restriction site and; (c) use of a Megaprimer approach.

pIX Fab phage display. Prior filamentous phage-based de novo human antibody libraries utilize pIII or pVIII phage coat proteins for display of desired proteins, with the exceptions of single Fv and scFV libraries (Gao et al., *Proc Natl Acad Sci USA*, 96: 6025-6030, 1999; Gao et al., *Proc Natl Acad Sci USA*, 99:12612-12616, 2002). The combination of pIX with the selected templates is a more efficient selection system for recovering Fabs that retain their selected properties upon conversion into mAbs and other related molecules.

Fab display. Unlike scFv, Fabs are natural segments of human antibodies and better recapitulate their biological activity when engineered into full antibodies. Efficient phage display of Fabs requires properties beyond good expression in a bacterial host. The V-region templates of the current invention were chosen for efficient phage display on filamentous phage, using a phage pIX protein.

Phagemid display. The Fab molecule is large relative to the phage pIX coat protein and may interfere with assembly of recombinant phage particles if linked to all pIX proteins produced in the bacterial cell. One approach to by-pass this interference is to use a pIX phagemid system, such described by (Gao et al., *Proc Natl Acad Sci USA*, 99:12612-12616, 2002), whereby both wild-type and Fab-linked pIX proteins can be incorporated into the recombinant phage particle. In a preferred application, libraries of the current invention are displayed by a pIX protein in a phagemid system.

Phage coat protein pIX for display. Like pIII, pIX is present at low copy number on the phage and is amenable to affinity selection of displayed Fabs. However, the pIII protein is critically involved in the infection process and proteins displayed on this protein can interfere with the efficiency of infection. Use of a pIX system helps avoid this problem. Moreover, either the heavy chain Fd or light chain segments can be fused to pIX for display. The libraries of the current invention displayed on the pIX protein are efficiently replicated and presented for selection and/or screening and provide an advantage over pIII-based systems.

Fab-pIX expression. One approach to screening proteins (e.g., Fabs) recovered from phage libraries is to remove the phage coat protein that is linked to the protein molecule for display. The small size of the pIX protein provides the option of production of screening of proteins such as Fabs directly without this additional step.

Design of the library scaffolds. The library scaffold is made from a set of human germline $V_H$ and $V_L$ genes. Analysis of the literature, as well as proprietary antibody information, led to the identification of the germline genes that represent the human IgG gene families, usage in the IgG repertoire, and the human antibody canonical structures. Optimal pairing between the $V_H$ and the $V_L$ and the probability of successful manufacture of antibodies derived from the selected germline genes were also considered in the analysis. The design of human natural and well paired $V_H$ and $V_L$ scaffolds is superior over the approach of using consensus human germline genes as the library scaffolds (Rothe et al. J. Mol. Biol. 376, 1182-1200 (2008) and more comprehensively represents the human repertoire (de Wildt et al. Nat Biotechnol 18, 989-994, 2000; Lee et al. J Mol Biol 340: 1073-93, 2004; Söderlind et al. Nat Biotechnol 18, 852-856, 2000 and Hoet et al. Nat Biotechnol 23, 344-348, 2005).

Expression and display ability of the library scaffolds. Efficient expression and display of Fab scaffolds more directly impact the quality of the library than the scaffold genes. The library scaffold Fab expression and the ability to display the scaffold were examined before library construction. Some scaffold Fabs that expressed or displayed poorly, or both, were excluded from the library construction. Use of well expressed and displayed library scaffolds helps ensure that a high proportion of the Fabs in the library are functional, and would likely be superior to libraries derived from combinatorial cloning of $V_H$ and $V_L$ genes that are genetically amplified from natural sources (Marks et al. J. Mol. Biol. 222, 581-59, 1991; Griffiths et al. EMBO J. 13, 3245-3260, 1994).

H-CDR3 Diversity. The library $V_H$-CDR3 was diversified in both length and sequence composition. About $10^9$ to $10^{18}$ total sequence possibilities depending on the lengths of the CDR were designed in $V_H$-CDR3 reflecting the importance of $V_H$-CDR3 in antigen binding. Unlike the use of all amino acid codons for amino acid diversification (e.g., NNK) and the use of exhaustive cloning methods to engineer $V_H$-CDR3 sequences from natural sources, we created $V_H$-CDR3 by using designed oligo-nucleotides that encode amino acid codons mimicking the amino acid usage pattern in human IgG repertoire (See Marks et al., J. Mol. Biol. 222, 581-59, 1991; Söderlind et al. Nat Biotechnol 18, 852-856, 2000 and Hoet et al. Nat Biotechnol 23, 344-348, 2005). The designed $V_H$-CDR3 contains fewer unwanted and unfavored amino acids (e.g., stop codons and cysteine) but a greater proportion of IgG like CDR3 sequences. The degenerate oligonucleotides can be used to create a large gene library in a mutagenesis reaction.

H-CDR1 and H-CDR2 Diversity. Amino acid diversity in $V_H$-CDR1 and $V_H$-CDR2 was designed to mimic the variations within germline sequences. The combined total sequence diversity in $V_H$-CDR1 and $V_H$-CDR2 ranges between about $10^2$-$10^5$. Combining this diversity with the large $V_H$-CDR3 sequence variation increases the overall diversity in the library which increases the probability of identifying antigen-binding antibodies. The unique design of the small, germline-like diversity favors discovery of germline or natural antibody-like sequences and minimizes the potential of isolating non-natural CDR combinations. This design is different from many other synthetic or semi-synthetic antibody libraries having larger sequence variations in all three $V_H$ CDRs (de Wildt et al. Nat Biotechnol 18: 989-994, 2000; Söderlind et al. Nat Biotechnol 18: 852-856, 2000; Rothe et al. J. Mol. Biol. 376: 1182-1200, 2008).

Diversity in Lc. The library light chains were designed with or without variation in the de novo library and Lc diversity also was introduced into the CDRs after Fabs were selected via phage panning. As the Lc diversity in the antigen binding Fabs is designed for binding affinity improvement, CDR positions that are frequently in contact with the antigen in antigen-antibody complexes of known structure were selected for diversification. The step-wised CDR diversification strategy effectively manages the large theoretic CDR sequence diversity and generates high affinity antibodies, more suitable for biological characterization.

Methods for library generation. A modified Kunkel mutagenesis method, generating billions of E. coli colonies each harboring a different Fab sequence, was used for the generation of the large Fab libraries. While efficient, the percentage of non-mutagenized parental DNA increases when generating highly complex sequence libraries. In addition, the technical limitation of synthesis of long oligonucleotides reduces the effectiveness of the method when used to make libraries containing sequence diversities in distant regions. To overcome these limitations, additional techniques of generating oligonucleotides greater than 350 bases were used. These techniques include use of a mega-primer and creation of a stem-loop sequence containing a restriction enzyme recognition site in the mutagenesis template in combination with the standard Kunkel mutagenesis method. Compared to other library technologies, such as restriction cloning (Marks et al. J. Mol. Biol. 222, 581-597, 1991; Griffiths et al. EMBO J. 13, 3245-3260 (1994); Hoet et al. Nature Biotechnology 23, 344-348, (2005), phage recombination (Gigapack, Invitrogen), and sequence specific recombination, the improved Kunkel based method is more effective in generating a sequence diverse library (greater than $10^9$) and is more versatile for introducing sequence diversity in any location in the targeted DNA.

In-line affinity maturation. An integrated affinity maturation process, or in-line affinity maturation, is designed to improve binding affinity of all Fabs selected from the libraries. As the libraries are strategically designed to leave the $V_L$ of the Fab invariant or at low diversity, additional antigen binding sites or interactions among CDRs should be readily created in $V_L$ via CDR sequence diversification. Improving the binding affinity of all Fabs after panning increases the success of identifying a functional antibody. The use of the Kunkel method for library generation enables the effective execution of the $V_L$ sequence diversification in a simple and continuous process. The design strategy and the technical advantages of the improved Kunkel mutagenesis method make the approach superior to other pooled maturation strategies where tedious library generation methods are employed that reduce the efficiency and benefit of the process (See Steidl et al. Mol. Immunol. 46, 135-144, 2008).

Parallel Library Panning. A semi-automated parallel panning process was developed to allow parallel selection of individual sub-libraries. The parallel panning increases the potential to discover a diverse set of antibodies. The coupling of parallel panning with in-line affinity maturation permits antibodies having a wide range of affinity to be improved simultaneously. Also, development of semi-automated panning allows systematic examination of different panning conditions to discover antibodies having desired properties.

Affinity Ranking. Affinity-based binding assays are used to screen the numerous, diverse and high affinity antigen specific antibodies to select the best binding antibodies for further characterization. Standard biochemical methods like ELISA and newer technologies for affinity measurement, for example, BIAcore (Biacore Biosystems), Octet (ForteBio) and BIND (SRU Biosystems), that are suitable for processing large number of samples are used alone or in combination for this purpose.

While having described the invention in general terms, the embodiments of the invention will be further disclosed in the following examples that should not be construed as limiting the scope of the claims.

EXAMPLES

Example 1

Display and Selection of Fab on pIX

Figure 3:
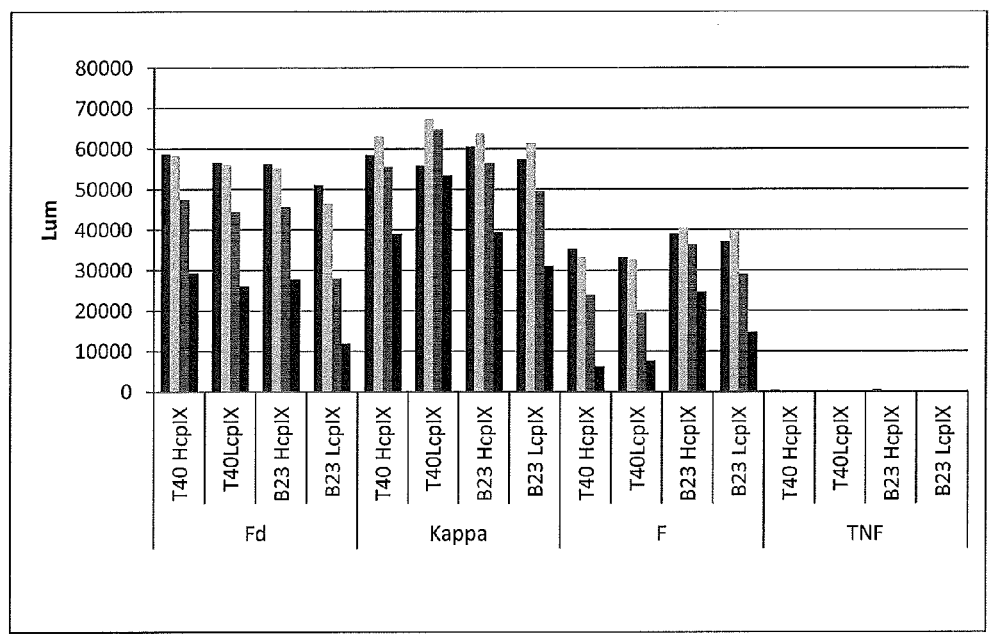
FIG. 3. ELISA showing the functional display of RSV Fabs T40 and B23 on phagemid particles by either Hc or Lc fusion to pIX. Serial 1:4 dilutions (left to right) of the phagemid particles were evaluated for binding to anti-Fd antibody, anti-kappa antibody, RSV F protein and an anti-TNF antibody as a negative control.

The vector, pCGMT9, (Gao et al., Proc. Natl. Acad. Sci. 96, 6025-6030, 1999), served as the backbone for the development of a phagemid vector capable of inserting heavy and light chain variable region segments in a Fab format for phage display via pIX fusion to the Fd or Lc fragments. FIG. 1 shows the features of the dual display and expression vector pCNTO-Fab-pIX, as designed for display of Fd linked to pIX. For light chain linked display, the Fd and Lc fragments are swapped such that Lc is fused to pIX and Fd is the soluble secreted fragment. Either phagemid vector can be converted to a Fab expression vector upon excising the pIX gene. To evaluate display via Fd or Lc, two different Fabs specific for the respiratory syncytial virus (RSV) F protein, Fab T40 (Tsui et. al., J. Immunolo. Meth. 263, 123-132, 2002) and Fab B23 (WO/2006/050280), were cloned into the pCNTO vectors. Both Fabs have kappa light chains. Cloned phage were generated for each construct. The pCNTO phagemid containing the Fabs was transformed into TG1 cells (Stratagene). A single colony was used to inoculate 2×YT/carb (2× yeast tryptone broth containing 100 ug/ml carbenicillin) plus 1% glucose and grown overnight with shaking at 37° C. The overnight culture was used to inoculate fresh 2×YT/carb at a 1:500 ratio and incubated with shaking at 37° C. until the culture reached an $OD_{600}$ nm of 0.5-0.6. The cultures were infected with helper phage (>$10^{11}$ pfu/ml) and incubated for 30 minutes at 37° C. without shaking. The infected culture was centrifuged and the cell pellet was re-suspended in 2×YT/carb containing kanamycin (50 µg/ml) and 0.5 mM IPTG (isopropyl-beta-D-thiogalactopyanocide). This induced culture was incubated at 30° C. overnight with shaking. The phage cultures were centrifuged and the media supernatant containing the phage was collected in fresh tubes. PEG and NaCl were added to a final concentrations of 2% and 0.25M, respectively, and each sample was incubated on ice for two hours with occasional mixing. The samples where then centrifuged and the supernatant discarded. The white pellet of precipitated phage was re-suspended in 2 ml 1×PBS. The re-suspended phage was centrifuged again, placed into new vials, and used in experiments or stored at −80° C. The phage sample was serially diluted at 1:10 intervals in 2×YT and the dilution series was spotted onto 2×YT (Carb/Glucose) agar plates to assess titer. TG1 cells grown to an $OD_{600}$ nm of 0.5-0.8 were added to each well containing the diluted phage and incubated for 30 minutes at 37° C. without shaking. A 2 µl sample from each infected well was spotted onto a dry LB/carb/1% glucose and LB/Kan agar plates and incubated overnight at 37° C. The spots containing clearly separated single colonies were counted (less than 10 colonies per spot). The recovered phage were evaluated in a phage ELISA for surface display of the heavy chain Fd or light chain via the pIX protein and for co-association of the corresponding soluble Lc or Fd fragment, respectively. The ELISA was designed to capture phagemid particles displaying Fd or Lc using plate wells coated with anti-Fd or anti-kappa antibodies followed by detection with an anti-M13 polyclonal antibody. As shown in FIG. 3, both T40 and B23 phagemid particles were captured by anti-Fd (The BindingSite) and anti-kappa (Southern Biotechnology) antibodies in either format of Fd or Lc fusion to pIX. This capture was specific because none of these phagemid constructs bound to wells coated with a control antigen (TNF). These results demonstrate that either Fd or Lc can be displayed by linkage to pIX and that the respective soluble Lc or Fd fragment co-associates with the displayed chain on the surface of the phagemid particle. The displayed Fabs were shown to bind to their specific antigen, the RSV F protein. The phage ELISA format was followed except that the plate wells were coated with the RSV antigen. As shown in FIG. 3, both Fabs specifically bound to the RSV F antigen in either Fd or Lc display formats. M13 helper phage, lacking any recombinant protein fused to its surface, was used as a control in the phage ELISA.

Example 2

Display and Selection of Fab Libraries on PIX for Affinity Maturation

The demonstration of display and efficient antigen-based enrichment of Fabs indicated that the pIX system could be applied to select variants from antibody libraries. Thus, Fab display using Fd linked to pIX was employed to search for variants of the B23 Fab with improved binding affinity. A library (P-1) was designed in which 4 amino acid residues in CDR1 of the light chain sequence were mutated to all other 19 amino acids using NNK as the codon at these positions. These positions are Y31, N32, I34, and Y36. The calculated possibility of variants at the amino acid level in P-1 is $1.6×10^5$, corresponding to $1.1×10^6$ variants in DNA.

Kunkel's single stranded mutagenesis method (Kunkel, Proc. Nat. Acad. Sci. 82: 448, 1985) was used to construct the P-1 library. Firstly, a plasmid template was created that contained stop codons in the region to be mutated so that any unmutated template contamination in the library will not produce parental Fab that could decrease the efficiency of the downstream selection process. The primers used to make the stop template for P-1 library were:

Plus strand:
(SEQ ID NO: 1)
GCG TCT CAG TCT GTT GAC <u>TAA TAA</u> GGT TAA TCT TAA
ATG CAC TGG TAC CAG CAG -continued Minus strand:
(SEQ ID NO: 2)
5' CTG CTG GTA CCA GTG CAT TTA AGA TTA ACC TTA TTA

GTC AAC AGA CTG AGA CGC

The underlined letters indicate stop codons. The reaction was carried out with pCNTO-B23-pIX using a QuickChange kit (Stratagene, Calif.).

To construct the P-1 Fab library with random mutation of the 4 amino acid residues within the variable region of the light chain of a Fab, an oligonucleotide was synthesized that had a 12 base pair (bp) degenerate NNK codon at each amino acid position. This oligonucleotide was flanked by two 18 bp nucleotide sequences identical to the regions preceding and following the region to be mutagenized. These primers are phosphorylated at the 5' end.

The sequences of the primers used for the P-1 library are

```
1. deg. LcCDR1 plus NNK:
                                    (SEQ ID NO: 3)
5'-Phos-GCG TCT CAG TCT GTT GAC NNK NNK GGT NNK

TCT NNK ATG CAC TGG TAC CAG CAG.

2. deg. LcCDR1 plus VNN:
                                    (SEQ ID NO: 4)
5' phos-GCG TCT CAG TCT GTT GAC NNK VNN GGT VNN

TCT NNK ATG CAC TGG TAC CAG CAG-3
```

To purify a single-stranded DNA template, a single colony of *E. coli* CJ236 harboring the template phagemid pCNTO-B23-pIX with stop codon was picked and put into 5 ml of 2YT growth medium with carbenicillin (50 μg/ml final concentration) and chloramphenicol (10 μg/ml). The culture was shaken at 200 rpm at 37° C. for about 6 hours. VCSM13 helper phage was added to a final concentration of $10^{10}$ pfu/ml without shaking, for 10 minutes. The culture was then transferred to 150 ml of 2YT with carbenicillin (10 μg/ml) and uridine (0.25 μg/ml) and incubated at 37° C. with shaking at 200 rpm overnight. The culture was centrifuged at 12,000 rpm for 5 min at 2° C. The supernatant was poured into a fresh tube, followed by addition of 1/5 volume of PEG/NaCl solution and incubated for 5 minutes at room temperature. The solution was then centrifuged for 10 minutes at 10,000 rpm (12,000 g) at 2° C. The phage pellet was resuspended in 2 ml of PBS and re-centrifuged for 5 minutes at 15,000 rpm at 2° C. Single stranded DNA was purified using a Qiagen QIAprep Spin M13 kit according to the manufacturer's instructions. The dU-ssDNA was quantified by UV absorbance. The yield was approximately 10 μg.

To anneal the degenerate oligonucleotide to the template, dU-ssDNA (8 μg) template was combined with phosphorylated oligonucleotide at a molar ratio of 1:10 (template:oligo) in a buffer containing Tris-HCl (50 mM, pH 7.5) and $MgCl_2$ (10 mM). The 250 μl reaction was incubated at 90° C. for 2 min., 50° C. for 3 min., and 20° C. for 5 min.

After the annealing reaction, 10 μl ATP (10 mM), 10 μl dNTPs (25 mM each), 15 μl DTT (100 mM), T4 ligase (30 units), and T7 DNA polymerase (30 units) were added and the reaction mixture was incubated at room temperature for 4 hours. The resulting DNA was purified, desalted, and dissolved in 35 μl of water. The dsDNA product was electroporated into *E. coli* TG-1 cells and the transformants allowed to grow overnight on agar plates containing ampicillin (100 μg/ml) and glucose (1%). The colonies were scraped off the plates in 2×YT medium and stored at −80° C. Based on the colony count, the library contained $6 \times 10^9$ members, 6000 times over the designed size.

To construct the phage library, an aliquot of 50 μl Fab-pIX phagemid library glycerol stock was inoculated into 25 ml SB/carb (100 μg/ml) and incubated at 37° C. with shaking at 250 rpm until the culture reached an $OD_{600}$=0.5-0.6. Cells were infected with 1 ml of VCSM13 helper phage (>$10^{11}$ cfu final concentration) and incubated for 45 minutes at 37° C. without shaking. Subsequently, the cells were centrifuged and re-suspended in 25 ml of SB/carb/kan (50 μg/ml)/0.5 mM IPTG and incubated at 30° C. with shaking at 250 rpm for 12-16 hrs. The phage library was harvested by 20% PEG/NaCl precipitation and the titer of the library was measured by spot titration. The library was aliquoted and stored at −80° C.

Three rounds of panning were performed with the P-1 Fab-pIX phage library using biotinylated F-protein antigen at concentrations of 10 nM, 1 nM, and 1 nM, respectively. Briefly, a 100 μl volume of phage library was blocked with 100 μl ChemiBlocker at room temperature for 1 hour in a pre-blocked 1.5 mL micro tube. Biotinylated F protein (10 nm) was added and the mixture was incubated at room temperature for one hour with occasional mixing, 10 μl of Streptavidin coated magnetic beads (Dynabeads M280 with a capacity of 5-10 μg of biotinylated IgG per 1 mg of beads) were added and the mixture was incubated with occasional stirring for 30 minutes at room temperature. The mixture was washed 10 times with incremental volumes of TBST from 1 ml to 10 ml followed by a 10 ml rinse with 1×TBS. A final rinse of 1 ml 1×TBS was performed. After the washing, bound phage were recovered by addition of 1 ml of freshly grown TG1 cells ($OD_{600}$=0.5-0.8) and incubation at 37° C. for 40 minutes without shaking. Then the cells were plated and grown overnight. The next day, the colonies on the spread plates were scraped using 2 mL of SB/carb/20% glycerol for each plate, and the sample was frozen at −80° C. An aliquot was used to initiate the culture for making a fresh phage library from these recovered colonies. The new phage library was used for additional rounds of panning as described above except the antigen concentration was decreased to 1 nM in round 2 and 0.1 nM in round 3.

After three rounds of panning, phagemid was prepared and the pIX gene was removed by digestion with NheI and SpeI restriction endonucleases. The linearized vector was purified by gel electrophoresis, extracted, self-ligated, and transformed into TG1 cells. Individual colonies from overnight growth on 2×YT/carb agar plates were picked into 96 deep well plates containing 0.5 ml of 2×YT/carb per well. The plate was incubated at 37° C. shaking until the culture reached an $OD_{600}$ nm of 0.7-1.0. IPTG was added to 0.5 mM and the plate was incubated at 30° C. with shaking overnight. The cultures were centrifuged and spent culture media was used for analysis. The supernatants were screened using a RSV F protein ELISA assay similar to that described in Example 1. Unique positive clones were identified by DNA sequence analysis and were used for scale-up production of purified Fab for further characterization.

For scale-up Fab production, a single colony was inoculated into 2×YT/carb/1% and grown overnight with agitation at 37° C. The culture was used to inoculate fresh 2×YT/carb/0.1% glucose at a 1:100 ratio. This culture was grown to an $OD_{600}$ nm of 1.0, Fab expression was induced by addition of IPTG to a final concentration of 0.5 mM, and the sample shaken overnight at 30° C. The cells were harvested from the expression culture by centrifugation. The cell pellet was resuspended in 1×PBS/350 mM NaCl/7.5 mM imidazole and complete protease inhibitor without EDTA (Roche) and lysed with a microfluidizer (3×). The lysate was centrifuged and the supernatant was centrifuged a second time. Talon® resin (Clonetech), equilibrated with 1×PBS, was added to the supernatant and mixed gently for two hours. The Fab-bound resin was collected by centrifugation and loaded onto a column. The resin was washed 2 times with 1×PBS/350 mM NaCl/7.5 mM imidazole and eluted with 150 mM EDTA/1× PBS. The eluate was dialyzed overnight against 1×PBS. The sample was concentrated by filter centrifugation (Centiprep-20, Amicon). Concentration was determined by $OD_{280}$ nm and purity was determined by SDS-PAGE and staining with Coommassie Blue.

Binding affinity to the RSV F protein was measured by ELISA and by BIAcore. The predominant substitutions recovered in phage selection were Y31L and N32F. Purified Fabs containing this combination had $K_D$'s ranging from 20 to 170 pM, a 9-68 fold improvement over the parental B23 Fab. In contrast, I34 was tolerant to many substitutions with a bias towards charged and polar amino acids, while no substitutions were selected at Y36. Additional libraries were constructed using the Kunkel's mutagenesis method and showed substitution efficiencies of 62% to 76%.

Other methods were evaluated for library construction. One approach was overlapping PCR with degenerate oligonucleotides (Stemmer, et al. Gene. 164, 49-53, 1995). All PCR reactions produced specific products that were suitable for restriction cloning and gave a low background of parent contamination. However, this method was less satisfactory than Kunkel's method because it had a lower efficiency of transformation.

Another approach was restriction endonuclease cloning. Two combinatorial libraries were made having defined mutations in both $V_H$ and $V_L$ regions. One library had a diversity of 1875, the other with a diversity of $2.5 \times 10^6$. The first library was made with more than 8,000 members; the second was made with more than $1.1 \times 10^7$ members. Thus, both libraries had more than 90% coverage of the designed diversity.

A gene synthesis approach was employed to combine B23 variants with improved affinity that were recovered from all the above described libraries. The V regions were synthesized with codon specific variation using GeneWriter® (U.S. Pat. No. 6,670,127). This library contained limited diversity at Hc-CDR2 positions I53L, K59Y, N62S, Lc-CDR1 positions Q27D, Y31FL, N32FLQ, I34KQRTV, Y36F, and Lc-CDR3 positions E97DA and D98H. Panning of this library was performed as described above with stringent washing conditions. A number of high affinity Fab clones were enriched and recovered. The affinity of these Fabs ranged from 2 to 25 pM, a more than 700-fold improvement over the 1.5 nM affinity of the B23 parent Fab. This improved affinity translated to an 8-44 fold improvement in viral neutralization in cell culture by the Fabs. The pIX Fd display system has been successfully applied to affinity maturation of several additional Fabs, with different antigen specificities.

Example 3

Fab De Novo Libraries

The efficiency of Fd display on the pIX coat protein, and its successful application to libraries for Fab affinity maturation, provided a rationale for extension of this methodology to de novo Fab libraries for isolation of antibodies to a variety of antigens.

3.1. Design Of Library Scaffolds. Human germline genes were selected as library scaffolds. A panel of germline $V_H$ and $V_L$ genes were initially identified based on the properties of 1) usage in known human antibody sequences; 2) canonical structure classes favoring protein and peptide antigen recognition; 3) biochemical and biophysical properties of antibodies derived from the germline genes; and 4) likelihood of forming of $V_H$ and $V_L$ hetero-dimers. Four (4) $V_H$ and four (4) $V_L$ germline genes best representing the properties listed above were selected. A single H-CDR3 sequence of 10 amino acids derived from a known antibody and the human JH4 segment were used in combination with each germline $V_H$ to generate complete $V_H$ genes domains. For the $V_L$, the Jk1 segment was recombined with each of the selected germline $V_L$ to generate full $V_L$ domains. FIG. 17 shows the sequences of the designed four $V_H$s and four $V_L$s (SEQ ID NO:s 5-12). The 4 $V_H$ and 4 $V_L$ scaffolds generated were combined with an IgG1 CH1 domain and a C-kappa domain, respectively, to constitute sixteen (16) recombinant human Fabs (FIG. 15; SEQ ID NOs: 18-49). Additionally, 4 $V_L$-λ germline scaffolds (1b, 1e, 2a2 and 3L) with C-lambda (SEQ ID NOs: 13-17, respectively) were combined with three of the $V_H$ scaffolds, 1-69 (SEQ ID NO:5), 3-23 (SEQ ID NO: 6) and 5-51 (SEQ ID NO:8).

Figure 4:
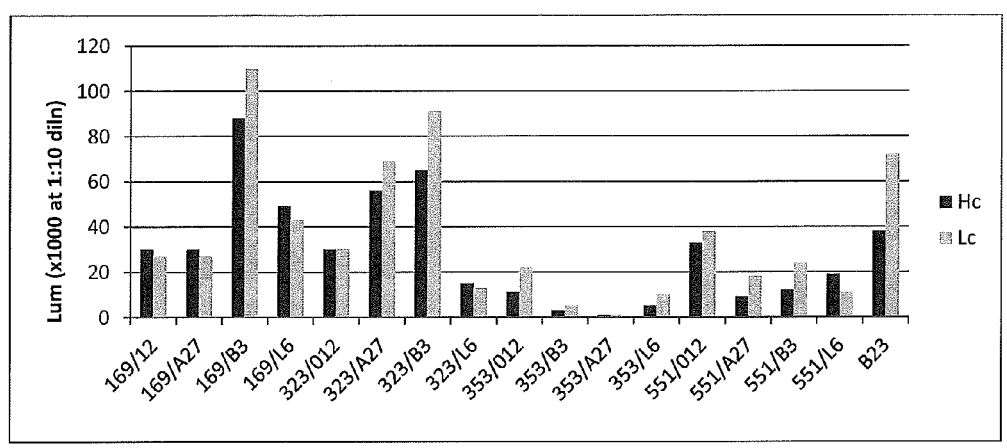
FIG. 4. ELISA demonstrating relative levels of phage display of the indicated heavy chain/light chain pairs.

3.2. Expression And Display Of The Library Scaffolds. The synthetic Fab DNA was cloned into the pCNTO-lacI-pIX vector (FIG. 1). $V_H$ scaffolds were cloned via the NcoI and ApaI sites. $V_L$ scaffolds, including the ompA signal sequence and sequences upstream were cloned via NheI and BsiWI sites (FIG. 1). Expression and display of the 16 scaffold Fabs were examined in a Western Blot analysis and in a phage ELISA, respectively. To examine display, phage was prepared as follows. A pCNTO-Fab-pIX-lacI construct was transformed into MC1061F' cells and grown over night in 2×Yeast Tryptone (2×YT)/Carbenicillin (Carb) (100 μg/ml)/Tetracycline (TET) (15 μg/ml)/1% Glucose medium at 37° C. with shaking. The next day, a portion of the overnight growth was used to seed 2×YT/Carb (100 μg/ml) and grown to an $OD_{600}$ of 0.6-0.8. The culture was then infected with VCSM13 helper phage for 40 minutes at 37° C. without shaking. The infected cells were spun down, resuspended in 2×YT/Carb (100 μg/ml)/TET (15 μg/ml)/Kan (35 μg/ml)/0.5 mM IPTG medium, and grown over night at 30° C. with shaking. The next day, cells were spun down and phage supernatant was collected and used for phage ELISA. The phage supernatant (neat), as well as 3 serial dilutions of 1:5, were added to ELISA wells coated with anti-Fd (Hc specific) or anti-kappa (Lc specific) antibodies. After incubation, unbound phage was washed away and the binding phage was detected using an anti-M13 antibody. All scaffold combinations except H3-53/L-B3 and H3-53/L-A27 bound to anti-Fd and anti-kappa antibodies, indicating sufficient display of both Hc and Lc on the phage surface (FIG. 4).

Figure 5:
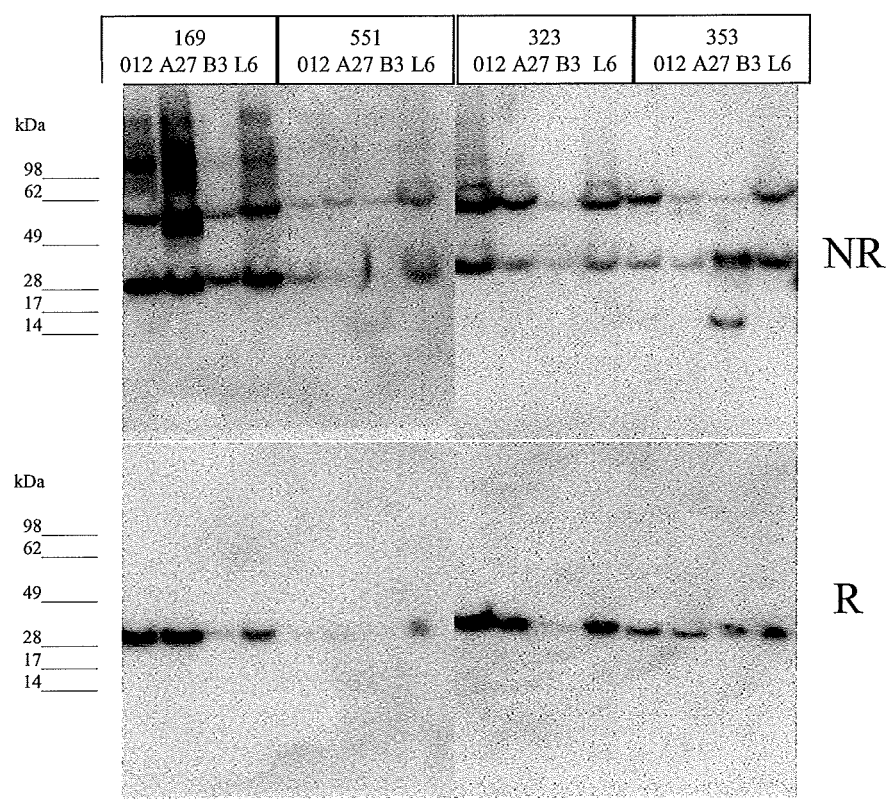
FIG. 5. Soluble expression of each Fab scaffold shown by Western blot analysis.

To examine Fab expression, the pIX gene is first excised from the pCNTO-Fab-lacI-pIX vector by SpeI and NheI restriction enzyme digestions followed by self-ligation of the digested vector DNA. This creates the Fab expression construct, pCNTO-Fab-lacI (FIG. 1). M1061F' cells harboring the pCNTO-Fab-lacI phagemid were grown overnight in 2×YT/1% glucose/Amp (100 μg/ml) medium at 37° C. with shaking. An aliquot of the overnight medium was used as an un-induced control. The overnight culture was inoculated into 2×YT/0.1% glucose/Amp (100 μg/ml) culture medium. The culture was grown at 37° C. with shaking to $OD_{600}$ nm 0.8-1.0. IPTG was added to a final concentration of 0.5 mM to induce Fab expression. The culture continued to grow for an additional 16-20 hours at 30° C. with shaking. The induced cultures were spun down and each cell pellet lysed by adding 0.4 mL BPER II reagent (Pierce). The supernatant of the spent cell lysate was collected and analyzed by Western Blot for Fab expression (FIG. 5). All Fabs expressed well at (>2 μg/ml), with the exception of those containing the B3 LC that expressed at about a 10-fold lower level.

3.3. Design of H-CDR3 Diversity. We designed large sequence diversities in H-CDR3 mimicking the repertoire of human antibodies. A total of 5,250 non-redundant and complete (including V region, CDR3 and framework 4) human antibody sequences were collected from various public sources. The data set contained all 7 $V_H$ families. Computer programs were used to extract CDR3 segments using the Kabat definition. The antibody sequences were further analyzed based on CDR3 length. The lengths of H-CDR3 ranged from 1 to 27 amino acids, and were shown as a normal distribution. The largest number of antibodies contained 12 amino acids in H-CDR3. Antibody sequences of the same length were aligned and grouped. The JH6 derived sequences were subtracted from the length groups to minimize the multiple consecutive tyrosine residues associated with the JH6 region. Computer programs were used to calculate amino acid distribution for each length. Residues at each position of the H-CDR3 length sequence group were sorted based on their frequency. A Weblogo (Crooks et al. Genome Research, 14:1188-1190, 2004) was used to plot a distribution of amino acids for each HCDR3 length. We chose CDR3 lengths of 7-14 amino acids for the library, which represents approximately 65% of the total human antibody repertoire. By analyzing the amino acid distribution among described human antibody CDR3 regions, we identified a pattern for each CDR3 length of 7-14 amino acids. FIG. 6 shows these patterns.

There is high amino acid diversity across H-CDR3 but amino acids glycine (G) and alanine (A) are frequently used in all positions. In addition, aspartic acid (D) is frequently used in position 95 and tyrosine (Y) is frequently encoded in the positions preceding the canonical region of the J segment. Amino acids phenylalanine (F), aspartic acid (D) and tyrosine (Y) predominate at positions 99-101. Since these positions often serve as structural support to H-CDR3 and are less accessible to antigen and/or to the surface of IgG, we fixed amino acids phenylalanine plus leucine (50/50 ratio) at position 99, aspartic acid at position 100 and tyrosine at position 101.

To mimic the highly diverse amino acid distribution in H-CDR3, we designed mixed-base oligonucleotides to encode H-CDR3 sequences for library construction. A procedure described by Wang & Saven (Nucleic Acids Res 30: e120, 2002) was used to determine the initial values of nucleotide mixture ratios at each position of a codon triplet in multiple random trials so that the coding amino acids derived from the codon triplets mimic the targeted amino acid distribution. In order to minimize the stop codons (<3%) and reduce the cysteine codon in the mix-base oligonucleotides, we further refined values of nucleotide mixture ratios at each position of a codon triplet using a script in Solver of MicroSoft Excel™ against the same target function as the Wang & Saven procedure (Nucleic Acids Res 30: e120, 2002). To simplify the process, two codon mixtures were designed to cover regions of similar sequence diversity, designated D and N. The nucleotide composition used for "D" and "N" positions are shown in FIG. 7. For the shorter H-CDR3 lengths of 7-8 amino acids, the NNS codon is used instead of the D or N mixtures.

We then generated mixed-base oligonucleotides based on the codon design. In addition to the D and N position, the tyrosine (~18%) rich positions otherwise share a similar amino acid distribution as the N positions. Separate oligos with N design codons at the N positions plus a fixed TAT codon at each tyrosine position were mixed with the N design codon oligos for libraries with CDR lengths of 11 to 14 amino acids. The ratio of N codon oligo and N plus TAT codon oligos for each Y position was about 7:1. Since the designer N codon has about 4.7% for tyrosine, this mixture results in an additional 13% tyrosine from the fixed TAT codon at all Y positions.

The oligos were used to construct the de novo Fab library using the methods layout shown in FIG. 7. DNA sequences from about 100 colonies from each sub-library were obtained and analyzed. Clones that were mutated from TAA stop codon in H-CDR3 of the template were considered positive clones. The translated H-CDR3 sequences were used to determine amino acid distributions at individual or combined D, N and Y positions. The result showed that the observed amino acid distribution at these positions closely mimicked the distribution found in the database and in the design (FIG. 8). Also, the designed mixed-base oligo mimicked the database amino acid distribution better than the NNS degenerate oligos.

3.4 Design H-CDR1 and H-CDR2 Diversity. We designed the diversity in H-CDR1 and H-CDR2 to mimic the human germline gene repertoire. H-CDR1 and H-CDR2 positions that were targeted for diversification were determined by 1) diversity in germline genes, (V base: http://vbase. mrc-cpe. cam. ac. uk/); and 2) frequency found in contact with antigen in antibody-antigen complexes of known structure (Almagro J Mol. Recognit. 17:132-143, 2004). The amino acid diversity at the selected positions was determined by 1) usage in germline (V base: http://vbase. mrc-cpe. cam. ac. uk/); 2) amino acids that are most frequently observed in human rearranged V genes (proprietary database); 3) amino acids predicted to result from single base somatic mutations of germline sequences; and 4) biochemical and biophysical properties of amino acids that contribute to antigen recognition. The combined sequence diversity in H-CDR1 and H-CDR2 ranged from $10^2$ to $10^5$. The usage frequency was used as a filter to restrict amino acids that are rare in rearranged human antibodies. This minimizes the non-natural sequence created by combinatorial mutations. Table 1 shows the design of H-CDR1 and H-CDR2 diversity.

TABLE 1

Heavy chain CDR 1 and CDR2 design

| | | Scaffold | | |
| --- | --- | --- | --- | --- |
| Loop | Position | 3-23 (SEQ ID NO: 6) | 1-69 (SEQ ID NO: 5) | 5-51 (SEQ ID NO: 8) |
| H1 | 31 | SDNT | S | SNT |
| | 32 | Y | Y | Y |
| | 33 | AGW | AG | W |
| | 34 | M | I | I |
| | 35 | SH | S | SG |
| H2 | 50 | VANG | GW | IR |
| | 51 | I | I | I |
| | 52 | SNKW | IS | YD |
| | 52a | YSGQ | PA | P |
| | 53 | SD | IY | GS |
| | 54 | G | FN | D |
| | 55 | SG | G | S |
| | 56 | S | T | DY |

3.5. Design Diversity In Lc. The following parameters were considered for designing light chain CDR diversity. First, we determined that the combined Lc diversity should not exceed $10^8$, as the Lc libraries were used in affinity maturation and were combined with a pool of approximately $10^2$ unique Hc clones derived from the phage selection during the first stage of panning the libraries. Therefore, the combined Hc and Lc complexity is about $10^{10}$, which can be effectively captured in a library generated by a single Kunkel's mutagenesis reaction. Second, we targeted positions frequently found in contact with the antigens in antigen-antibody complexes of known structure or so-called Specificity-Determining Residues (SDRs; Almagro *J Mol. Recognit.* 17, 132-143, 2004). These positions 30-32, 50 and 91-94, for L-CDR1, L-CDR2 and L-CDR3, respectively. Third, position 96 was also variegated because it is encoded in the Joining (J) genes and all five human J genes differ at that position. Fourth, as in the design of H-CDR1 and H-CDR2 (Table 1), we minimized the sequence diversity that is not likely to occur in nature by choosing the germline encoded amino acids that are frequently found in the rearranged human V regions at the positions to be diversified. Finally, we evaluated the biochemical and biophysical properties of the amino acids suitable for antigen binding at the given positions and complemented the V germline gene diversity with those amino acids to reach the $10^8$ criteria. The individually designed Lc-CDR diversities are shown in Table 2a.

TABLE 2a

Light chain CDR design.

| Loop | Position | Scaffold | | | |
|---|---|---|---|---|---|
| | | O12 (SEQ ID NO: 10) | L6 (SEQ ID NO: 11) | A27 (SEQ ID NO: 9) | B3 (SEQ ID NO: 12) |
| L1 | 30 | SRNAD | SRNAD | SRNTD | YSHFA |
| | 30a | — | — | SNR | S |
| | 30e | — | — | — | KTNE |
| | 31 | SNKDG | NSKD | SNRADH | K |
| | 32 | YHNDWFSAV | YWDFHSAN | YFHQSEK | YFHNWDAS |
| L2 | 50 | FYTNKADG | ADKGYFTN | ADGS | WSRDYA |
| L3 | 91 | SAYHPD | RYSGF | YSHA | YSHA |
| | 92 | FIYHNDKGRE | RHNSL | YNDSHIFKG | YNDSHIFKG |
| | 93 | STHNDRG | NDKR | SNTDGHR | SNTDGHR |
| | 94 | TYLVFSRGPI | WA | TYLVFAS | TYLVFAS |
| | 96 | LWRFYIN | WYFLIR | WYFLIR | WYFLIR |

TABLE 2b

Design of Lambda Lc Libraries

| Loop | Position | Scaffold | | | |
|---|---|---|---|---|---|
| | | 1b (SEQ ID NO: 13) | 1e (SEQ ID NO: 14) | 2a2 (SEQ ID NO: 15) | 3L (SEQ ID NO: 16) |
| L1 | 29 | | GATND | | STNR |
| | 31a | NS | | GS | |
| | 31b | | DG | | |
| | 31c | | HN | ND | |
| | 32 | YTA | | YLR | |
| | 34 | SN | | | SN |
| L2 | 50 | DESR | GSAD | ED | |
| | 51 | ND | SN | | |
| | 52 | ND | | | SN |
| | 53 | KQ | NHY | NK | |
| L3 | 89 | GA | | | |
| | 90 | TA | | | |
| | 92 | | | TA | |
| | 93 | SD | SNRTI | SG | SNTG |

TABLE 2b-continued

Design of Lambda Lc Libraries

| Loop | Position | Scaffold | | | |
|---|---|---|---|---|---|
| | | 1b (SEQ ID NO: 13) | 1e (SEQ ID NO: 14) | 2a2 (SEQ ID NO: 15) | 3L (SEQ ID NO: 16) |
| | 94 | | SNRT | | SGT |
| | 95a | SN | SHN | SN | DN |
| | 95b | AG | GAV | TN | |
| | 95c | DHSGAFNL | SHPL | FLSPYHVAE | |
| | 96 | "ABC" | "AB" | "ABC" | "ABC" |

Definition of the three ABC codons for each scaffold:
1b:
"ABC" is defined as three separate codon designs:
A = ACGT (10, 10, 70, 10; 10, 16.1, 41.5, 32.4; 10, 44.3, 10, 35.7)
B = ACGT (0, 0, 0, 100; 100, 0, 0, 0; 0, 50, 0, 50)
C = ACGT (0, 0, 0, 100; 0, 0, 100, 0; 0, 0, 100, 0)
1e:
"AB" is defined as three separate codon designs:
A = ACGT (1.6, 6.0, 9.1, 83.2; 67, 28.4, 2.4, 4.2; 0, 50.7, 0, 49.3)
B = ACGT (7.4, 0, 42.9, 49.7; 1.3, 0.3, 57, 41.4; 0, 0, 100, 0)
2a2:
"ABC" is defined as three separate codon designs:
A = ACGT (11.8, 49.7, 33.4, 5; 7.8, 5, 26.8, 60.4; 37.1, 5, 52.9, 5)
B = ACGT (0, 0, 0, 100; 50, 0, 0, 50; 0, 0, 0, 100)
C = ACGT (0, 0, 0, 100; 0, 0, 100, 0; 0, 0, 100, 0)
3L:
"ABC" is defined as three separate codon designs:
A = ACGT (8.5, 36.6, 17, 37.5; 0.8, 26.1, 52, 21.1; 0, 4.3, 95.4, 0.3)
B = ACGT (5, 15, 5, 75; 100, 0, 0, 0; 0, 50, 0, 50)
C = ACGT (0, 0, 100, 0; 0, 0, 0, 100; 0, 0, 100, 0)

An overlapping PCR method (Stemmer, et al. Gene. 164, 49-53, 1995) was used to generate the $V_L$ scaffolds containing the designed diversities at the specific positions described in Tables 2a and 2b. Several oligonucleotides with specific codons encoding the amino acid diversity at targeted SDRs for variation were synthesized. These oligonucleotides were then mixed to generate a library of variants used to amplify double strand DNA (dsDNA) by overlapping PCR. $V_L$ fragments encoding the Framework region (FR)-1, L-CDR1-2 mutated regions and the FR-3-L-CDR3 mutated region were combined, and complete $V_L$ domains were synthesized in an additional PCR reaction with flanking amplification primers. This reaction produced a full length $V_L$ library with sequence variations in all three L-CDRs at the desired positions. Alternate DNA synthesis methods may be used to synthesize individual $V_L$ libraries according to the designs described herein, such as those methods described in U.S. Pat. No. 6,670,127 and other methods known to those skilled in the art.

3.6. Methods For Library Generation. Three sets of libraries were constructed to probe sequence diversity for isolating high affinity antibodies to a broad spectrum of targets. One set of libraries, called V2.0, contained the combinatorial pairing of the twelve scaffolds and focused the diversity on $V_H$ by keeping the $V_L$-κ scaffolds in the germline configuration. Another set of libraries, called V3.0, included the additional diversity of $V_L$-κ scaffolds. The third set of libraries, V4.0, contained the combinatorial pairing of the 3 $V_H$ scaffold libraries (SEQ ID NOs: 5, 6, and 8) with 4 $V_L$-λ germline scaffolds (1b, 1e, 2a2 and 3L; SEQ ID NO:s 13-16, respectively).

A modified Kunkel's single stranded mutagenesis method (Kunkel et al. Methods Enzymol 154, 367-382, 1987) was used to make individual libraries based on each scaffold Fab. To minimize the effect of the non-mutagenized scaffold Fab template on the final library function, the TAA stop codon and XhoI site was inserted into the H-CDR3 region of the templates. Single strand DNA of each stop codon-containing template was prepared in the CJ236 strain of *E. coli*. Oligos, each encoding the designed H-CDR1 and CDR2 diversity, were used simultaneously as primers in a DNA polymerization reaction using T7 DNA polymerase and T4 ligase. The reaction mixture was used to transform MC1061F' competent cells, yielding typically greater than $10^9$ independent colonies per library construction. Sequence analysis of randomly picked clones following the Kunkel mutagenesis reaction showed that 31% to 55.7% of the clones sequenced had mutations in H-CDR1 and/or H-CDR2 regions. The percentage of clones with both H-CDR1 and H-CDR2 mutations were found to be equal to or higher than that of clones having mutations in only one CDR region.

Figure 9:
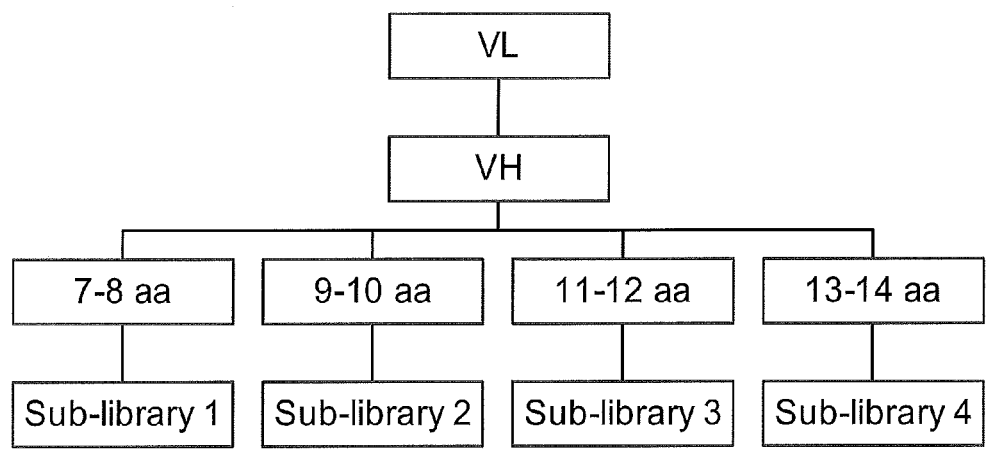
FIG. 9. Summary diagram of library architectures.
Figure 10:
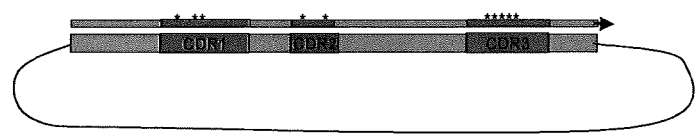
FIG. 10. Schematic of mega-primer targeting the entire segment of a V region.
Figure 11:
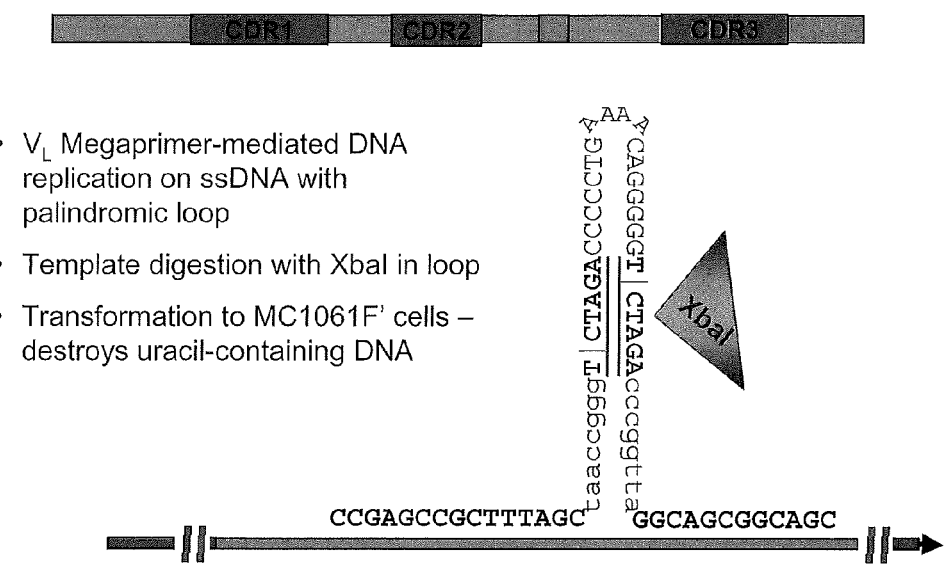
FIG. 11. Schematic of palindrome assisted parental strand elimination.

The colonies were scraped from plates to inoculate fresh media, double strand plasmid DNA was prepared and used to transform CJ236 cells. The transformed cells were infected with helper phage, and single strand DNA was prepared from overnight cell culture and was used as a reaction template to introduce H-CDR3 diversity via our mixed-base designed degenerate oligonucleotides. A library for each Fab scaffold/template was individually constructed. The 8 different lengths of H-CDR3 were constructed in four reactions. H-CDR3 length 7-9 and 10-11 and 12-14 amino acids were grouped, respectively. DNA was transformed into MC1061F' cells to yield approximately $10^{10}$ transformants per H3 length. Double stranded DNA was prepared from an aliquot of each library and the $V_H$ library was digested with XhoI to eliminate all parental clones. DNA was pooled from each H3 length library and transformed into MC1061F' cells to $10^{10}$ transforming units (tu) per $V_H/V_L$ combination. Cells were grown in 500 mL 2×YT (Carb/Glucose) until OD=0.8. One tenth of the cells were infected with 1 mL of VCSM13 helper phage ($10^{13}$ cfu/mL) for 30 minutes at 37° C. and incubated overnight at 30° C. in 2×YT (Carb/IPTG/Kan). The remainder of the transformed cells were pelleted and re-suspended in 50 mL 2×YT (Carb/20% glycerol) & stored at −80° C. as glycerol stocks. Phage was precipitated with PEG/NaCl and re-suspended in PBS, yielding a titer of $10^{12}$ cfu/mL. The resulting panel of libraries containing diversity in $V_H$, combined with $V_L$-κ germline scaffolds was named V2.0. FIG. 9 shows the library architecture.

The short oligonucleotide used in the step-wise Kunkel reactions during library generation reduced efficiency of the method. We generated mega-primers covering all three targeted CDRs to be sequence diversified by overlapping PCR and used them in mutagenesis reactions. This allows all combinatorial sequence diversification to be accomplished in one reaction, which is more efficient than the step-wise reactions using shorter oligonucleotides. For example, we generated $V_L$ library fragments by overlapping PCR and/or by chemical synthesis using GeneWriter™ and used them as mega-primers for hybridization mutagenesis.

For construction of the V3.0 library, V2.0 $V_H$ diversity was combined with designed diversity in the selected $V_L$-κ scaffolds, using PCR-based mutagenesis of each $V_L$ scaffold. Overlapping PCR was used to generate the $V_L$ containing the designed diversities at the desired positions. We isolated a megaprimer from the overlap PCR by use of a biotinylated reverse primer ($V_L$ Term Bio: 5'-CGTACGTTTAATTTC-CACTTTGGTGCCC SEQ ID: NO 50). The dsDNA PCR product was captured on Dynal Streptavidin M280 beads and the ssDNA forward strand was isolated by denaturation with 150 mM NaOH. Megaprimer was then precipitated with LiCl and ethanol and reconstituted in $dH_2O$ Single stranded DNA was isolated from each V2.0 library and used as template DNA for Kunkel's mutagenesis with the Lc megaprimers. Megaprimer was annealed to the template ssDNA, then, T7 DNA polymerase and T4 DNA ligase were added, and the reaction was incubated for two hours at 20° C., two hours at 15° C., followed by heat inactivation at 65° C. for 20 minutes and stored at 4° C. dsDNA was transformed into MC1061F' cells to give $10^{10}$ transformants per $V_H/V_L$ pair. This produced a mutation rate of about 30-40% for each $V_L$, with mutations in all three CDRs of $V_L$.

As noted above, the current Kunkel's method often eliminates un-mutated, parental ssDNA only to a 20-50% range when constructing a highly complex sequence library. To further reduce the parental DNA, a palindromic sequence containing two XbaI restriction sites, TAACCGGG TCTAGACCCCCTGAAAACAGGGGG TCTAGACCCGGTTA (SEQ ID: NO 51) was engineered into the targeted mutagenic sequence regions, e.g., $V_H$ and/or $V_L$. During the annealing of the primer to ssDNA, the palindrome forms a double stranded step-loop structure and the mutagenic primer spans this palindrome by hybridization to flanking sequences. DNA replication proceeds from the annealed primer using T7 DNA polymerase. Closed circular DNA is generated by T4 DNA ligase. This product is digested with the restriction endonuclease at its site (XbaI) within the palindromic loop, thus nicking the parental DNA strand and destroying its in vivo replicative potential. The combined palindrome sequence elimination and the Kunkel's method reduce the parental DNA by greater than 95%, a significant improvement over the current Kunkel method alone. We inserted one palindrome into the $V_L$ and another with a different restriction site into the $V_H$, thus creating a double-loop vector ($V_H$-loop/$V_L$-loop). The V3.0 L6-$V_L$ library was constructed using a double loop vector where a L6-library megaprimer was applied via Kunkel's mutagenesis and parental DNA was digested with XbaI within the engineered palindromic loop. Application of heavy chain megaprimers to the ssDNA from this L6-library, followed by restriction digestion of the parental $V_H$-loop, yielded the final V3.0 L6 set of libraries. We termed this method, "megaprimer hybridization and digestion mutagenesis."

To generate the V4.0 library with the 3 $V_H$ scaffold libraries combined with 4 $V_L$-λ germline scaffolds, designed diversity in the $V_H$ domains of the 1-69, 3-23 and 5-51 scaffolds was applied to the $V_L$-λ germline scaffolds. We employed the megaprimer hybridization and digestion mutagenesis methodology for generation of this library. A palindromic loop with an AscI site (underlined), AGGGTTA GGCGCGCCT-GGTCGCAAAAGCGACCA GGCGCGCCTAACCCA (SEQ ID: NO. 52) was inserted into the "framework 3" region of each $V_H$ scaffold paired with each $V_L$-λ germline scaffold. Megaprimers for $V_H$ diversity were generated by overlap PCR. A fragment from framework 1 to framework 3 was amplified from the V2.0 kappa Lc library to capture designed diversity in H-CDR1 and H-CDR2. A fragment from framework 3 to the end of framework 4 was generated using the oligonucleotides described for H-CDR3 mutagenesis along with the $V_H$-Library Reverse primer (5'-TGGTGCTTTTGCTGCTCGGC (SEQ ID: NO. 53)). The fragments were gel purified (Qiagen Gel Extraction) and digested with DpnI to eliminate any contaminating plasmid template DNA. These fragments were then joined together by overlapping PCR with biotinylated $V_H$-Library Reverse primer and $V_H$-Library Forward primer (5'-CTG-GTTTGTTATTACTCGCG (SEQ ID: NO 54). Megaprimer was prepared as discussed above and applied to ssDNA from the $V_H$-loop/$V_L$-λ vectors for hybridization mutagenesis. Following DNA replication, DNA was purified via phenol/chloroform extraction and precipitation with LiCl, glycogen & ethanol. DNA was then digested with XbaI to nick the parental strand within the engineered palindromic loop. DNA was purified via phenol/chloroform extraction and precipitation with LiCl, glycogen & ethanol and re-suspended in $dH_2O$. This library DNA was then transformed into MC1061F' cells to greater than $10^9$ transformants per mutagenesis reaction.

In-line maturation libraries were also designed for the $V_L$-λ germline scaffolds according to the same criteria as for the $V_L$-κ libraries (FIG. 17). Libraries were generated from pools of designed and degenerate oligonucleotides by amplification of $V_L$ fragments followed by overlap PCR. Each $V_L$ library fragment was cloned into a phagemid vector by megaprimer hybridization and digestion mutagenesis as described. Libraries were transformed into MC1061F' cells to $10^9$ transformants per library. Plasmid DNA was extracted from cells to be used for cloning of $V_H$ regions from antibodies selected from the de novo V4.0 library.

3.7. Parallel library panning. Since our libraries are designed and constructed in such a way that each sub-library can be used individually based on the HC or LC scaffold, we designed parallel panning strategies to pan individual as well as sub-pooled library sets to maximize the chance of identifying diverse binding antibodies.

Bovine Serum Albumin (BSA) and Hen-Egg White Lysozyme (HEL) were chosen as model antigens for library validation. We pooled the 1-69 and 3-23 HC framework sub-libraries into 4 sub-sets by keeping the LC framework separate for parallel panning. As a comparison, we also pooled all sub-libraries of 1-69 and 3-23 HC and their associated LC into one pool and used it to pan against BSA. Streptavidin paramagnetic beads (Dyal), coated with biotinylated antigen, were incubated with phage for one hour at room temperature. Binding and washing steps were performed in a high throughput format in a 96 well block using a KingFisher instrument (ThermoFisher). After several washing steps, bound phage were eluted and amplified by infecting MC1061F' cells for the next round of selection (see Example 2). After four rounds of selection, phagemid DNA was isolated, the pIX encoding segment was removed by restriction digestion, and the phagemid was ligated and transformed into MC1061F' to express soluble Fabs. Single clones were isolated and tested for Fab expression and antigen binding by ELISA. Fab expression was detected by incubating Fab containing cell extracts on an anti-Fd coated ELISA plate followed by detection with an anti-kappa light chain antibody conjugated with HRP. Antigen specificity was tested by capturing biotinylated antigens on streptavidin-coated plates with the subsequent addition of cell lysates containing Fabs. For the competitive ELISA, an excess of soluble non-biotinylated antigen was included to compete Fab binding to the immobilized biotinylated antigen. Bound Fab was detected using anti-kappa conjugated HRP.

The benefit of parallel panning of the libraries is evident in the percentage of positive binding clones after panning. Results of parallel panning showed 30 of 90-screened clones (33% hit rate) bound to BSA, relative to a 7% hit rate when panning was done with a pooled library (Table 3). Although there is no direct comparison of two panning strategies for Lysozyme, where only a completely pooled library panning was performed, the 4% hit rate is similar to that obtained for BSA with the pooled library. (Table 3).

TABLE 3

Summary Of BSA And Lysozyme Panning Results

| | Total Screened | Bind to Ag |
|---|---|---|
| BSA | | |
| Sub Pool: Individual 4 LC | 90 | 30 (33%) |
| Complete Pool | 180 | 12 (7%) |
| HEL | | |
| Complete Pool | 180 | 7 (4%) |

Sequence analysis identified six unique Fabs for BSA and three for Lysozyme as shown in FIG. 18.

Unique BSA and HEL binders were purified to determine binding affinity ($K_D$). A two-step Fab purification procedure was used to purify the Fabs. E. coli lysates were first subjected to a single step IMAC procedure. After dialysis, the IMAC column eluate was subjected to a second purification step, anion exchange using QFF Sepharose resin, which improved the purity of the Fab to about 90%.

BIAcore analysis was used to determine the affinity of the six BSA and three Lysozyme binders. The binding affinities of the Fabs ranged from 0.1 to 28 nM for BSA binders and 6-260 nM for Lysozyme binders, respectively. These Fabs were specific as shown by their lack of binding to the non-selecting antigen (BSA or lysozyme) or to the reference surfaces (empty, activated, and blocked CM5 matrix). Tables 4 and 5 show the binding kinetics of the BSA and the HEL Fabs.

TABLE 4

Activity Of Purified Fab And Their Apparent $K_D$ Of Binding To BSA (40 RU)

| Fab | $k_a \times 10^5$ $M^{-1}s^{-1}$ | $k_d \times 10^{-3}$ $s^{-1}$ | $K_D$ (nM) | $R_{max}$ (RU) |
|---|---|---|---|---|
| C2 (Hc/Lc) (SEQ ID NO: 55/56) | 0.60 (3) | 1.69 (1) | 28 | 4* |
| C6 (Hc/Lc) (SEQ ID NO: 57/58) | — | — | NB | NB |
| D6 (Hc/Lc) (SEQ ID NO: 59/60) | 5.72 | 1.95 (1) | 4 | 40 |
| D11 (Hc/Lc) (SEQ ID NO: 61/62) | 56.16 (2) | 0.53 (1) | 0.09 | 44 |
| F4 (Hc/Lc) (SEQ ID NO: 63/64) | 0.51 (2) | 0.48 (1) | 9 | 10* |
| F6 (Hc/Lc) (SEQ ID NO: 65/66) | 4.3 (1) | 11.3 (1) | 26 | 43 |

NB: no binding

TABLE 5

Activity Of Purified Fab And Their Apparent $K_D$ Of Binding To Lysozyme (10 RU)

| Fab | $k_a \times 10^5$ $M-1s-1$ | $k_d \times 10^{-3}$ $s-1$ | $K_D$ (nM) | $R_{max}$ (RU) |
|---|---|---|---|---|
| E5 (Hc/Lc) (SEQ ID NO: 67/68) | 2.27 (1) | 2.33 (1) | 10 | 51 |
| E7 (Hc/Lc) (SEQ ID NO: 69/70) | 4.6 (1) | 120 (2) | 260 | 50 |
| E8 (Hc/Lc) (SEQ ID NO: 71/72) | 4.24 (2) | 2.49 (1) | 6 | 50.5 |

Figure 13:
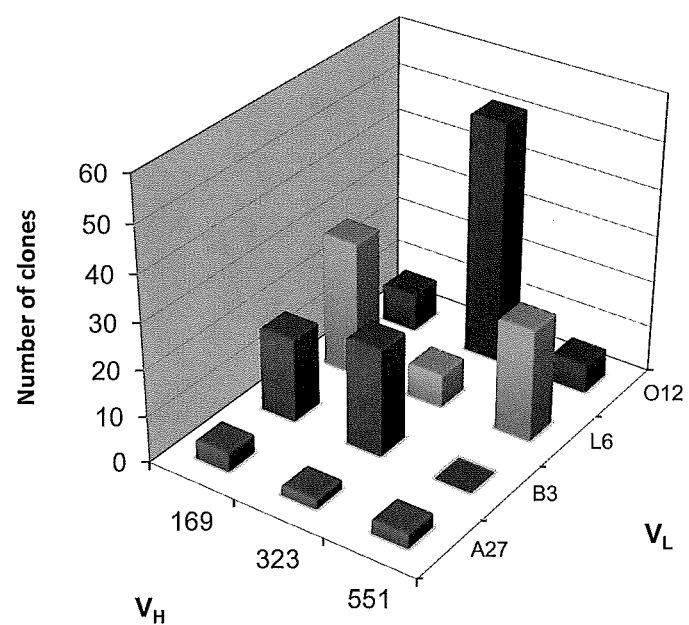
FIG. 13. Distribution of $V_H$ and $V_L$ scaffolds recovered by panning the libraries against a panel of proteins.

3.8. Extended Panel of Targets. To test further the ability of the libraries to generate specific binders against diverse targets, six varied protein antigens were utilized: mMCP-5 (9 kD), mTF ECD (25 kD), hTNFα (35 kD; trimer), hIgE (150 kD), hIgG (150 kD) and hColagen II (300 kD; triple helix). After three rounds of selection, a total of 169 unique Fabs were isolated from the libraries. All the $V_H$ and $V_L$ scaffolds except 3-53 used in assembly of the libraries, were recovered in the selections (FIG. 13). $IGV_H$ 3-23 was the most commonly selected $V_H$ scaffold, consistent with panning results from antibody libraries displayed on pIII (Hoogenboom, Nat Biotechnol 23: 1105-16, 2005) and analyses of human gene usage in natural antibodies (de Wildt et al., J Mol. Biol. 285: 895-901, 1999). However, the prevalence of $IGV_H$-3-23 was skewed by the high number of $IGV_H$-3-23 Fabs isolated against hIgE (see below). Excluding the anti-hIgE Fabs, $IGV_H$-1-69 is the most prevalent scaffold. For $V_L$, the most frequent scaffolds observed in the recovered Fabs were IGVK-L6 and IGVK-O12. Both genes encode the same canonical structure class that is commonly used for protein recognition. Fabs containing the IGVK-A27 gene, frequently observed in human antibodies and thus often used in design of phage display libraries (de Wildt et al. Nat Biotechnol 18: 989-994, 2000), were seldom found.

Figure 14:
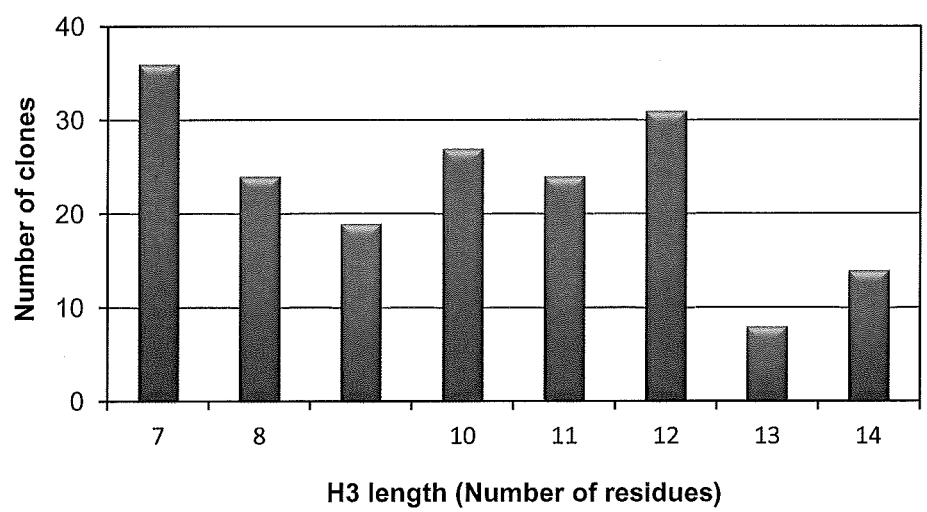
FIG. 14. Distribution of H3 loop lengths in selected clones.

FIG. 14 shows the distribution of H3 loop lengths in the selected clones. All designed lengths were observed. The H3 length distribution resembles a bimodal model, with a peak at 12 amino acids, which is the average length observed in human sequences, and another peak at seven residues. Most of the sequences contributing to the peak in the seven-residue length were isolated against a single antigen, (hCollagen II). Thus, the short H3 loops recovered in the analyzed clones might reflect the structure of a dominant epitope in hCollagen II. Further analysis of the library output on different antigens may allow correlation of structural features at the antigen-binding site with antigen types, leading to development of antigen-focused libraries as has recently described for haptens (Persson et al. J Mol. Biol. 357: 607-620, 2006) and peptides (Cobaugh et al. J Mol. Biol. 378: 622-633, 2008).

The recovery frequency of each $V_H$ scaffold after selection is stratified by antigen specificity in Table 6. Some antigens showed highly-skewed scaffold selections. For mMCP-5, all Fabs isolated from the V2.0 libraries, and the majority isolated from the V3.0 library, contained the $IGV_H$-5-51 scaffold. For hIgG, no Fabs were recovered from the V2.0 libraries and only Fabs bearing $IGV_H$-1-69 were isolated from the V3.0 libraries. The hIgG antigen was a humanized antibody with mouse CDRs and human germline gene frameworks. Library pannings with this antigen were conducted in the presence of 20% human serum to guide selection of anti-CDR Fabs. Isolation of anti-idiotypic Fabs from the V3.0 libraries only, along with epitope-specific antibodies from V3.0 selected to another protein (data not shown), suggests that epitope specificity can be gained through diversification of $V_L$. This is consistent with a recent report by Liang and co-workers (J Mol. Biol. 378: 622-633, 2007) showing added benefit from diversifying $V_L$ for de novo selection of antibodies.

The number of unique clones isolated against the indicated antigen is shown for each $V_H$ scaffold in Table 6. The number in parentheses is the number of clones with diversified $V_L$ regions isolated from panning the V3.0 libraries.

TABLE 6

Performance of V2.0 and V3.0 libraries.

| $V_H$ Scaffold | Library | | | | | | Affinities |
|---|---|---|---|---|---|---|---|
| | V2.0 | | | V3.0 | | | |
| | 1-69 | 3-23 | 5-51 | 1-69 | 3-23 | 5-51 | (nM) |
| TNFα | 4 | 5 | 1 | 12 (9) | 1 (1) | 0 | ND |
| mMCP-5 | 0 | 0 | 17 | 1 (1) | 0 | 4 (4) | 0.2-20 |
| mTF | 1 | 9 | 2 | 7 (7) | 5 (5) | 2 (2) | 4-20 |
| IgE | 4 | 39 | 2 | ND | ND | ND | ND |
| Collagen II | 7 | 19 | 2 | 10 (10) | 3 (1) | 5 (5) | 5-18 |
| IgG* | 0 | 0 | 0 | 7 (7) | 0 | 0 | 0.4-8 |

The Fab affinities for the antigens are summarized in the last column of Table 6. For hIgG and MCP-5 Fabs, the affinities ranged from 0.4 nM to 8 nM and from 0.2 to about 20 nM, respectively. For mTF, two Fabs had affinities of 5 nM and 20 nM; and for Collagen II, two Fabs had affinities of 5 nM and 18 nM. These results are comparable to antibodies isolated from pIII display libraries based on different rationales, including semi-natural (Hoet et al. Nat Biotech 23: 344-348, 2005), synthetic single-(Lee et al. J. Mol. Biol. 340: 1073-1093, 2004) and multiple-scaffold (Rothe et al. J. Mol. Biol. 376: 1182-1200, 2008) libraries.

Figure 12:
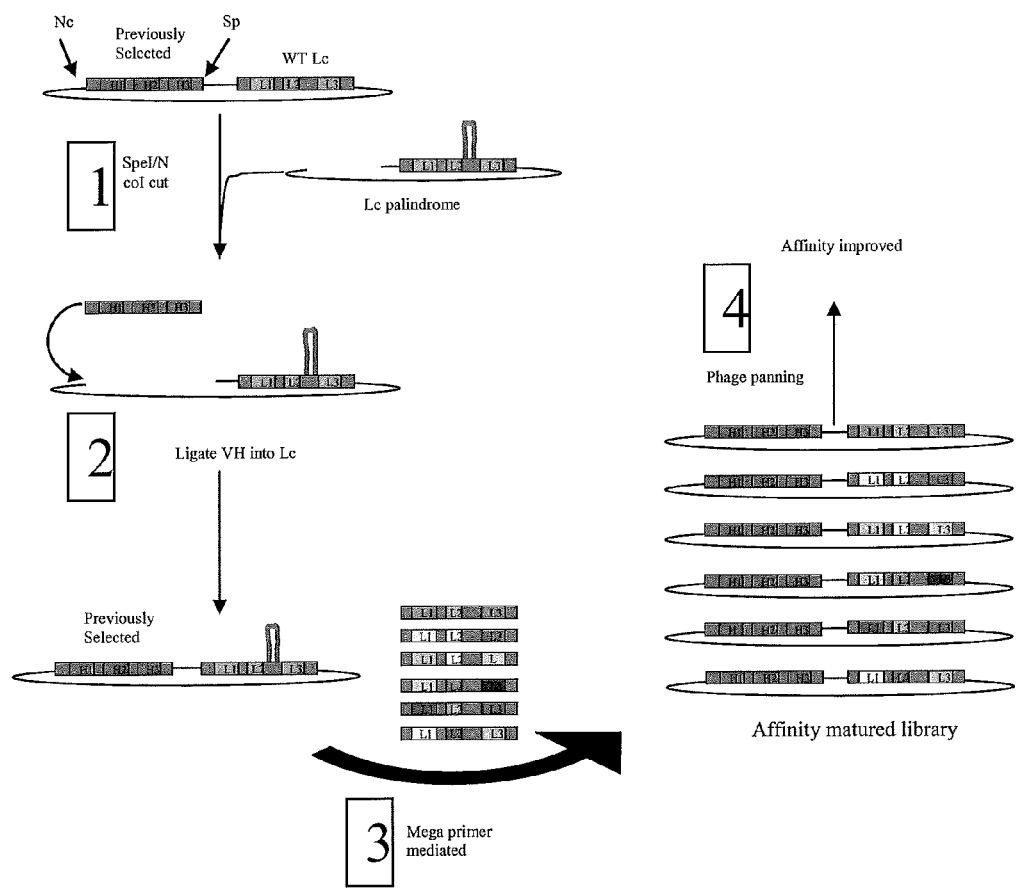
FIG. 12. Schematic of in-line affinity maturation.

3.9. In-Line Affinity Maturation. We designed the affinity maturation of the binders selected from the de novo library as part of the phage panning process, and named the process "in-line maturation." The process starts with a pool of binding Fabs, with or without detailed characterization, followed by the diversification of CDR sequences in the Lc of the original binders, which were derived from one of the four germline Lc used as the library scaffolds. The Lc CDR diversities will create additional binding activities that can be selected via further phage panning. The process is described below and schematically in FIG. 12. First, the $V_H$ regions of lead antibodies isolated through panning of the Fab de novo library were sub-cloned into $V_L$-palindromic loop vectors. Single stranded DNA (ssDNA) of these vectors was prepared for hybridization mutagenesis with the $V_L$ library megaprimers or other suitable methods described herein. For example, the combined palindrome sequence elimination and the mega primer Kunkel's mutagenesis method can be used efficiently to generate the $V_L$ diversified secondary library for the in-line affinity maturation. Parental DNA was eliminated by XbaI digestion and by subsequent transformation into the non-permissive host strain. This method allowed for highly efficient creation of a library covering designed sequence diversities. Another approach to diversifying the Lc of the lead antibodies is to sub-clone the $V_H$ regions into a Lc library already constructed in the pCNTO-Fab-lacI-pIX vector.

A phage library was then made by infecting the mutational library with helper phage. Next the library was subjected to additional rounds of panning with higher selection stringency to enrich binders with improved binding affinity over the binders selected initially from the primary library. These selections include lowering antigen concentrations, increasing wash time and frequency. Alternatively, binding competitors or other binding stress components, e.g. altering binding temperature and adding detergents, can be included into the binding and/or washing buffer to select binders with desired properties. Other biochemical and biophysical conditions suitable for use in phage binding and subsequent *E. coli* infection can also be included in the panning. After panning, DNA was recovered from the phage. Fabs were expressed and subjected to binding as well as other biochemical, biophysical and biological characterizations. DNA recovered from the phage can be cloned directly into IgG vectors. In this case, mAb instead of Fab will be expressed and characterized. For example, we have generated $V_L$ library fragments by overlap PCR methods and used them as megaprimers for hybridization mutagenesis. The mega-primer was produced by PCR and the minus strand was amplified with a biotinylated primer (See Example 3.6). The biotinylated strand was captured on streptavidin magnetic beads (Dynal) and the unbiotinylated strand was purified by denaturation in 0.15M NaOH. The eluted strand was then used for megaprimer-mediated DNA replication on ssDNA. The $V_H$ regions of lead antibodies isolated through panning the Fab de novo library were subcloned into $V_L$-Loop vectors. These selected $V_H$/$V_L$-Loop vectors were made into ssDNA for hybridization mutagenesis with the $V_L$ library megaprimers. Elimination of parental DNA, as noted by loss of the XbaI-containing palindrome, was determined by sequencing randomly picked library clones. The efficiency of mutagenesis of the three CDRs to a library of variants was 75%. This method allowed for highly efficient creation of a library of $4 \times 10^8$ variants. We have seen similar results for the creation of libraries in the other 3 $V_L$-k chains used in the Fab de novo library. Libraries were transformed to $2 \times 10^8$ and phage was made to $10^{11}$ cfu/mL.

To test the in-line maturation process with the antibodies selected against the extended panel of targets (Example 3.9), two anti-mTF Fabs and two anti-IgG Fabs, all from the V3.0 de novo library, were selected as case studies. The $V_H$ regions of two anti-IgG Fabs, called F17 and F19, were cloned into the L6 library to yield libraries of about $10^7$ clones. The anti-mTF $V_H$ regions of two Fabs, F10 and F11, were cloned into the O12 and B3 libraries, respectively, with the same yield as the L6 libraries. After selection using stringent panning, several unique clones were identified for each Fab (FIG. 16). For the anti-IgG clones we were able to improve affinity from 10 to 100 fold for F17 and 3 to 10 fold for F19. In all the cases a significant improvement in the off-rate was observed, making these Fabs tractable for cell-based and in vivo studies. For the anti-mTF F10 clone the affinity was improved five-fold from 20 pM to 4 pM, most significantly in off-rate. Similar results have been obtained for clones isolated from the V2.0 library. Therefore, this facile step to improve the affinity of selected Fabs demonstrates the ability of the pIX display platform to select and mature high affinity antibodies while enabling rapid optimization of antibodies suitable for in vivo studies or therapeutic applications.

There is a need for synthetic antibody libraries and methods that simultaneously deliver the elements of human therapeutic antibodies of high affinity and activity, high productivity, good solution properties, and a propensity of low immune response when administered in humans. There is a further need to increase the efficiency of antibody isolation from synthetic libraries, relative to current methods, to reduce the resource costs of antibody discovery and accelerate delivery of antibodies for biological evaluation. The libraries and methods of this invention meet these needs by coupling comprehensive design, assembly technologies, and phage pIX Fab display.

What is claimed:

1. A method for screening a phage library for Fab antibody fragments having a desired biological activity, comprising (a) expressing Fab antibody fragments in said phage library wherein said fragments are expressed in bacterial host cells, and where said host cells comprise a recombinant nucleic acid phage vector comprising the sequence of SEQ ID NO:79, and nucleic acid sequences encoding a phage pIX protein fused to a Fab amino acid sequence, wherein said Fab amino acid sequence binds to an antigen and (b) selecting bacterial cells expressing said Fab antibody fragments having said desired biological activity.

* * * * *